US007326692B2

(12) United States Patent
Ashton-Rickardt et al.

(10) Patent No.: US 7,326,692 B2
(45) Date of Patent: Feb. 5, 2008

(54) INDUCTION OF IMMUNITY USING INHIBITORS OF GRANZYMES

(75) Inventors: Philip G. Ashton-Rickardt, Chicago, IL (US); Joseph T. Opferman, Brookline, MA (US)

(73) Assignee: The University of Chicago, Chicago, IL (US)

( * ) Notice: Subject to any disclaimer, the term of this patent is extended or adjusted under 35 U.S.C. 154(b) by 926 days.

(21) Appl. No.: 09/993,363

(22) Filed: Nov. 14, 2001

(65) Prior Publication Data
US 2003/0148511 A1 Aug. 7, 2003

(51) Int. Cl.
*A61K 48/00* (2006.01)
*C12N 15/63* (2006.01)
*C12N 15/74* (2006.01)

(52) U.S. Cl. .................... 514/44; 424/93.21; 424/93.2; 424/93.1; 435/320.1; 435/325; 435/455

(58) Field of Classification Search ............... 424/93.1, 424/93.2, 93.21; 514/44; 435/320.1, 325, 435/455
See application file for complete search history.

(56) References Cited

U.S. PATENT DOCUMENTS

2002/0127698 A1* 9/2002 Geiben Lynn et al.

OTHER PUBLICATIONS

Romano et al. Stem Cells 2000; 18:19-39.*
Cullen (2001) Nature, vol. 7(1), 20-21.*
Bird et al., "Selective Regulation of Apoptosis: the Cytotoxic Lymphocyte Serpin Proteinase Inhibitor 9 Protects against Granzyme B-Mediated Apoptosis without Perturbing the Fas Cell Death Pathway," *Mol. Cell. Biol.*, 18:6387-6398, 1998.
Bird, "Regulation of pro-apoptotic leukocyte granule serine proteinases by intracellular serpins," *Immunol. Cell Biol.*, 77:47-57, 1999.
Bladergroen et al., "The granzyme B inhibitor, protease inhibitor 9, is mainly expressed by dendritic cells and at immune-privileged sites," *J.Immunol.*, 166:3218-3225, 2001.
Brodie et al., "In vivo migration and function of transferred HIV-1-specific cytotoxic T cells," *Nat. Med.*, 5(1):34-41, 1999.
Clay et al., "Efficient transfer of a tumor antigen-reactive TCR to human peripheral blood lymphocytes confers anti-tumor reactivity," *J.Immunol.*, 163:507-513, 1999.
Clay et al., "Potential use of T cell receptor genes to modify hematopoietic stem cells for the gene therapy of cancer," *Path.Onc. Res.*, 5:3-15, 1999.
Froelich et al., "New paradigm for lymphocyte granule-mediated cytotxicity," *J.Biol.Chem.* 271:29073-29079, 1996.
GenBank Accession No. AF200209, 2000.
GenBank Accession No. U71364, 1996.
GenBank Accession No. U96700, 2001.
Kam et al., "Granzymes (lymphocyte serine proteases): characterization with natural and synthetic substrates and inhibitors," *Biochim Biophys Acta*, 1477(1-2):307-323, 2000.

Matloubian et al., "A role for perforin in downregulating T-cell responses during chronic viral infection," *J.Virol.*, 73:2527-2536, 1999.
McMichael and Rowland-Jones, "Cellular immune responses to HIV," *Nature*, 410:980-987, 2001.
McMichael, "Preparing for HIV vaccines that induce cytotoxic T lymphocytes," *Curr. Opin. Immunol.*, 10:379-381, 1998.
Nagahara et al., "Transduction of full-length TAT fusion proteins into mammalian cells:TAT-p27$^{KIP1}$ induces cell migration," *Nature Medicine*, 4:1449-1452, 1998.
Ober et al., "Affinity of thymic self-peptides for the TCR determines the selection of CD8$^+$ T lymphocytes in the thymus," *Int Immunol*, 12:1353-1363, 2000.
Opferman et al., "Differentiation of cytotoxic T cell memory," *The 30$^{th}$ Annual Meeting of Japanese Society for Immunology*, Abstract S6-3, 113, Sep. 2000.
Opferman et al., "Linear differentiation of cytotoxic effectors into memory T lymphocytes," *Science*, 283:1745-1748, 1999.
Opferman et al., "Suicide induced by cytolytic activity controls the differentiation of memory CD8+ T lymphocytes," *Int Immunol*, 13(4):411-419, 2001.
Poncet et al., "Antifection: an antibody-mediated method to introduce genes into lymphoid cells in vitro and in vivo," *Gene Therapy*, 3:731-738, 1996.
Schwarze et al., "In vivo protein transduction: delivery of a biologically active protein into the mouse," *Science*, 285:1569-1572, 1999.
Sun et al., "A Cytosolic Granzyme B Inhibitor Related to the Viral Apoptotic Regulator Cytokine Reponse Modifier A Is Present in Cytotoxic Lymphocytes," *J. Biol. Chem.*, 271(44):27802-27809, 1996.
Sun et al., "A New Family of 10 Murine Ovalbumin Serpins Includes Two Homologs of Proteinase Inhibitor 8 and Two Homologs of the Granzyme B Inhibitor (Proteinase Inhibitor 9)," *J. Biol. Chem.*, 272(24):15434-15441, 1997.
Talanian et al., "Granule-mediated killing:Pathways for granzyme B-initiated apoptosis," *J.Exp Med.* 186:1323-1331, 1997.
Tan et al., "Rapid death of adoptively transferred T cells in acquired immunodeficiency syndrome," *Blood*, 93(5):1506-1510, 1999.

(Continued)

*Primary Examiner*—Anne M. Wehbe
(74) *Attorney, Agent, or Firm*—Fulbright & Jaworski L.L.P.

(57) ABSTRACT

The present invention provides methods for enhancing host immunity to a virus and/or a cancer and methods for enhancing the cytotoxic T-cell (CTL) mediated immune responses by providing granzyme B inhibitors to a subject. One objective of the invention is to induce long-term protective immunity to a subject in need thereof This is accomplished by providing granzyme inhibitors to the subject which increase the number of memory-CTLs and thereby prevent or alleviate viral infections and/or treat. Providing granzyme inhibitors is also effective in the prevention of cancers. Some examples of granzyme inhibitors contemplated within the present invention include the endogenous serpins such as SPI6 and PI9, other suicide substrates of granzyme B, granzyme B antibodies, etc. Also provided are methods for expression of nucleic acids encoding granzyme inhibitors in cytotoxic T-lymphocytes (CTLs).

30 Claims, 11 Drawing Sheets

OTHER PUBLICATIONS

Trapani et al., "Proapoptotic functions of cytotoxic lymphocyte granule constituents in vitro and in vivo," *Curr. Opinions in Immunology,* 12:323-329, 2000.

Walden and Eisen, "Cognate peptides induce self-destruction of CD8+ cytolytic T lymphocytes," *Proc. Natl. Acad. Sci. USA.,* 87:9015-9019, 1990.

Wu-Hsieh et al., "Virus induced immunosupression: a murine model of suspetability to opportunistic infection," *J.Infect.Dis.,* 158:232-235, 1988.

Zhumabekov et al., "Improved version of a human CD2 minigene based vector for T cell-specific expression in transgenic mice," *J. Immunol. Methods,* 185:133-140, 1995.

Borrow et al., "Virus-induced immunosuppression: immune system-mediated destruction of virus-infected dendritic cells results in generalized immune suppression," *J. Virol.,* 69:1059-1070, 1995.

Ciurea et al., "Persistence of lymphocytic choriomeningitis virus at very low levels in immune mice," *Proc. Natl. Acad Sci USA,* 96:11964-11969, 1999.

Klenerman and Zinkernagel, "What can we learn about human immunodeficiency virus infection from a study of lymphocytic choriomeningitis virus," *Immunological Reviews,* 159:5-16, 1997.

Odermatt et al., "Virus-triggered acquired immunodeficiency by cytotoxic t-cell-dependent destruction of antigen-presenting cells and lymph follicle structure,"*Proc. Natl. Acad Sci USA,* 88:8252-8256, 1991.

Zinkernagel, "Immunity, immunopathology and vaccines against HIV," *Vaccine,* 20:1913-1917,2002.

* cited by examiner

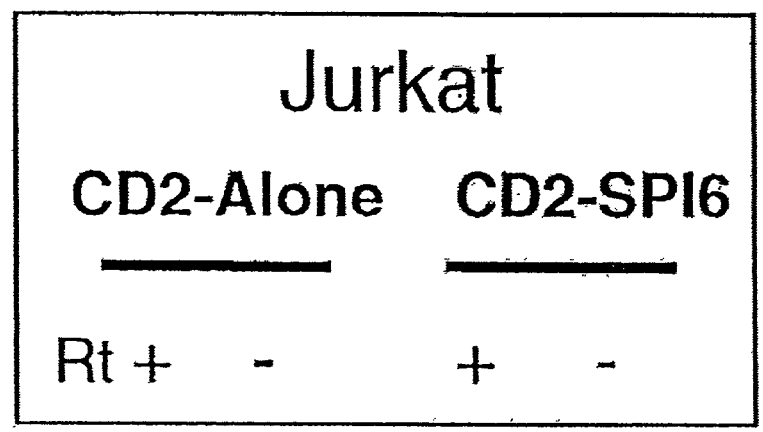
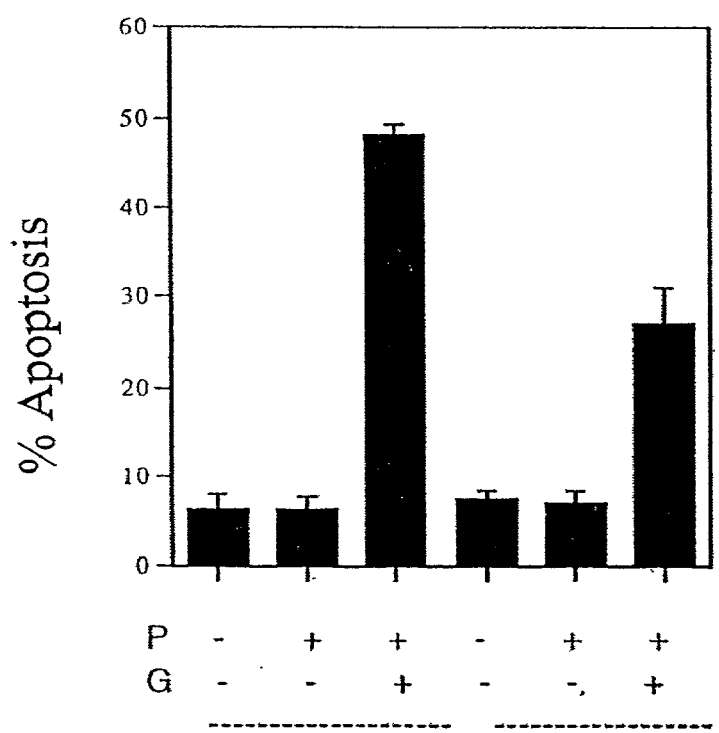
FIG. 2 a
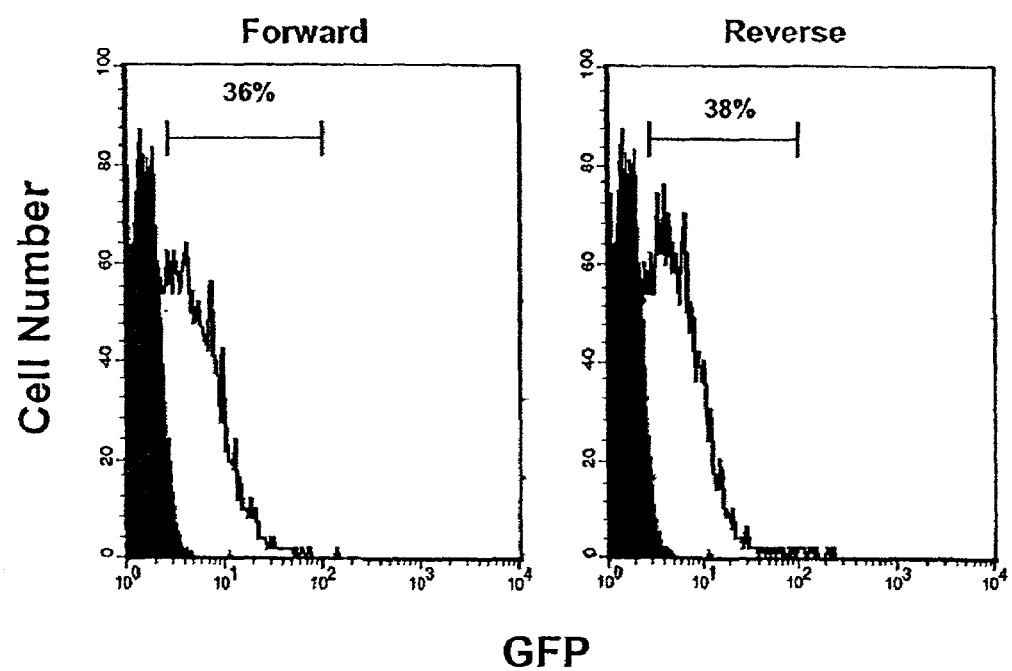
b
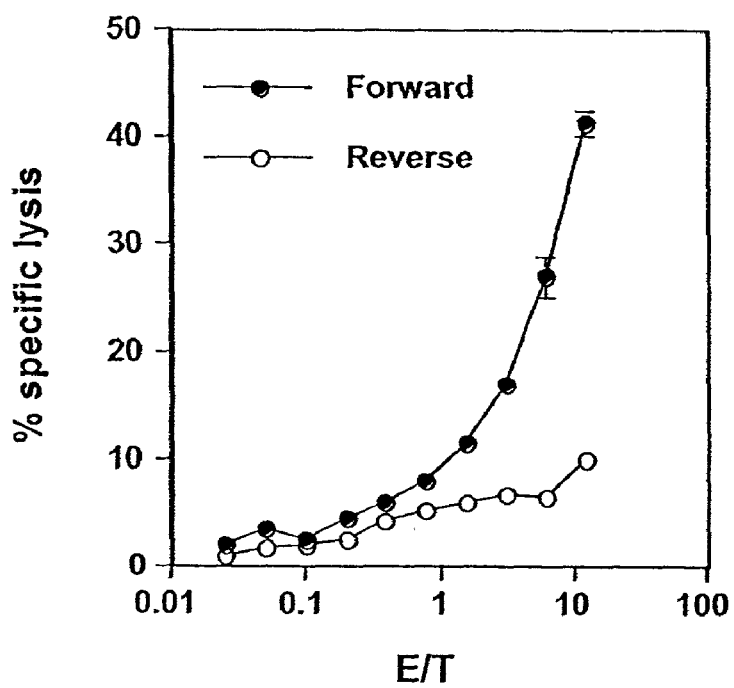
FIG. 5 A-B

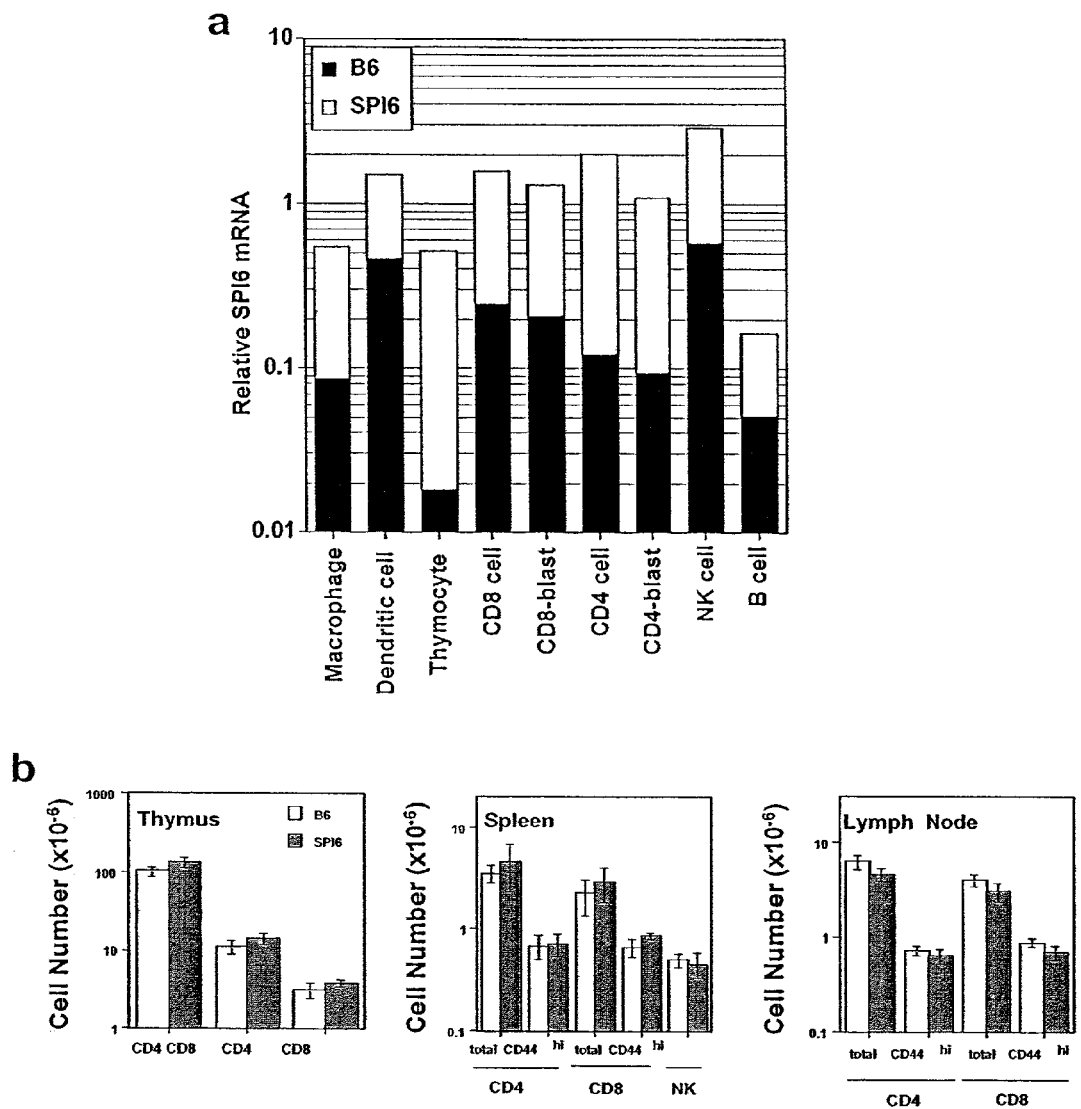
FIG. 6 A-B

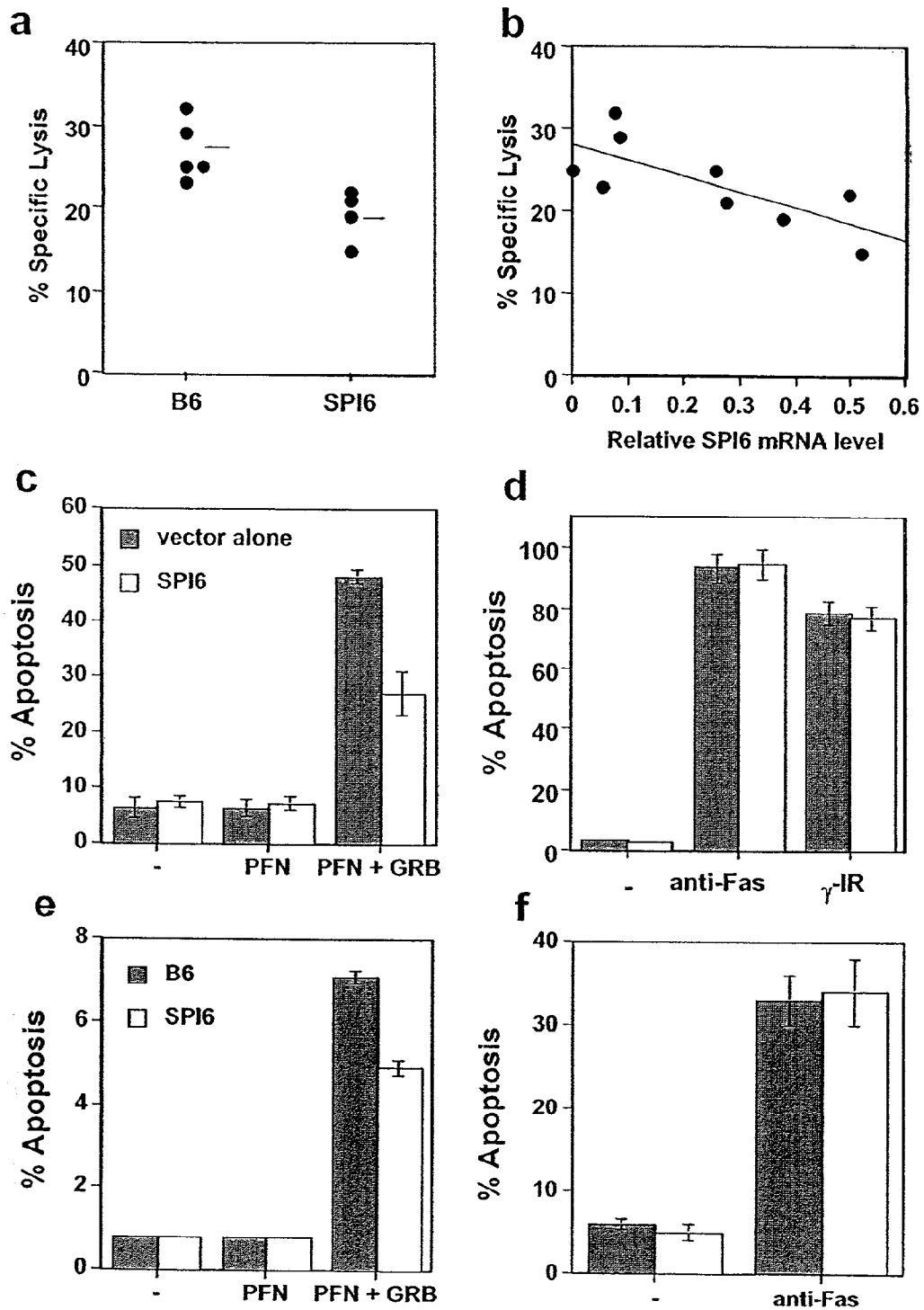
FIG. 7A-F

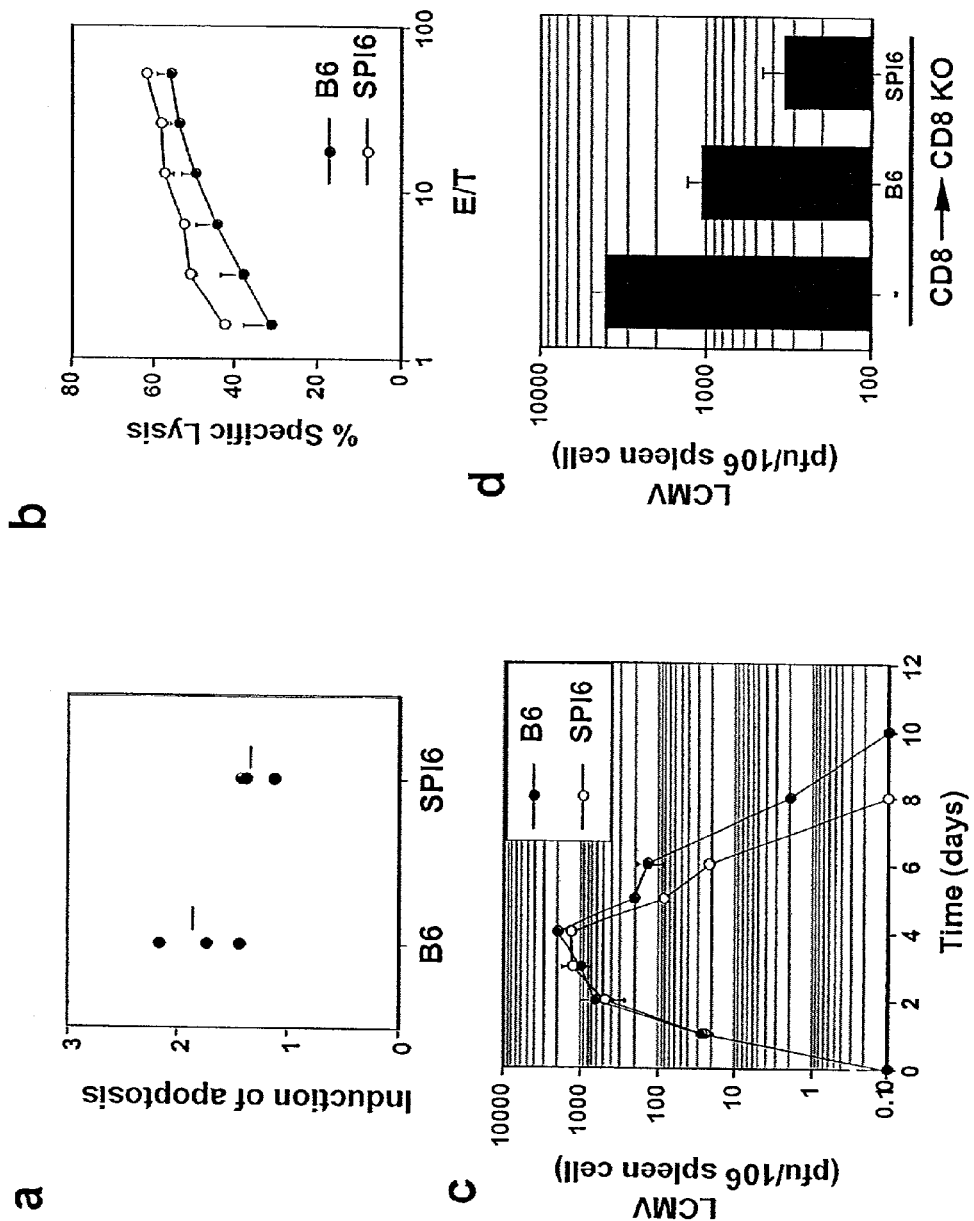
FIG. 8 A-D

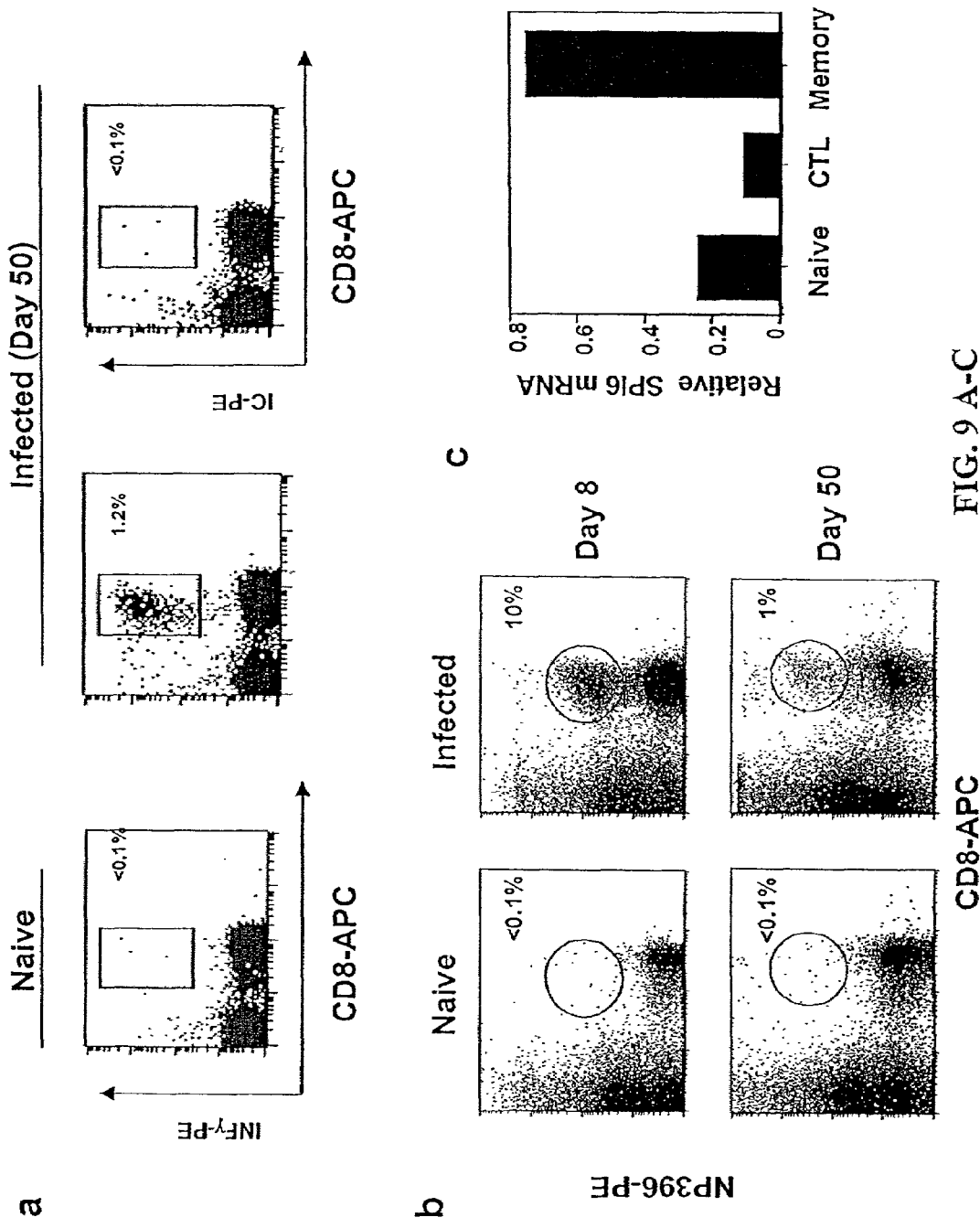
FIG. 9 A-C

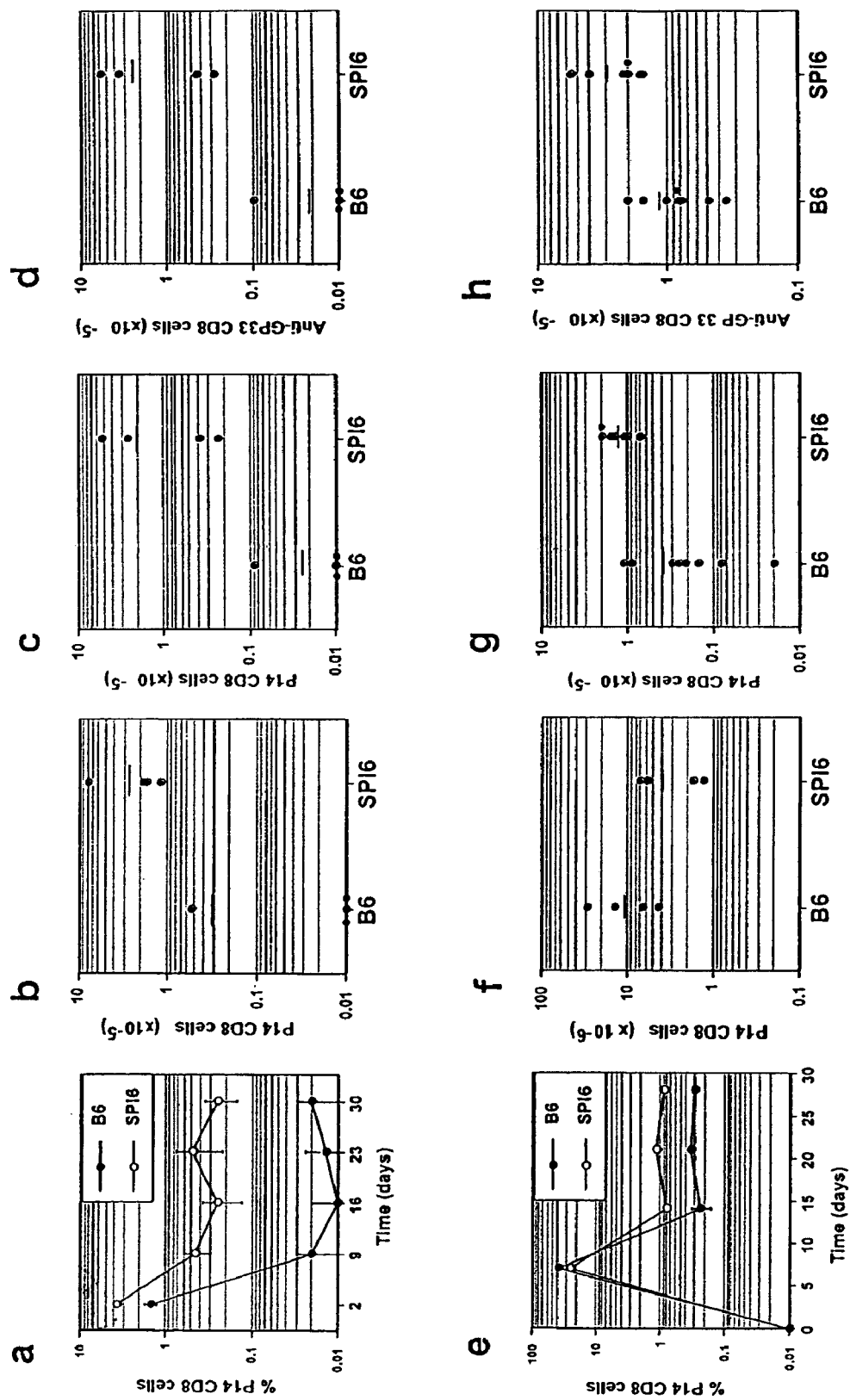
FIG. 11 A-H

INDUCTION OF IMMUNITY USING INHIBITORS OF GRANZYMES

The government owns rights in the present invention pursuant to grant numbers R01 AI45108 and R01 AI40608 from the National Institutes of Health.

BACKGROUND OF THE INVENTION

1. Field of the Invention

The present invention relates generally to the fields of immunology, viral diseases and cancer immunity. More particularly, it concerns the induction of immunity to viruses or cancers by the expression of nucleic acids encoding a granzyme inhibitor in cytotoxic T-lymphocytes (CTLs) or by the provision of a granzyme inhibitor to a CTL. Specifically, the invention provides methods for the induction of immunity, methods for the induction of long-term protective immunity, and methods for preventing and alleviating chronic viral infections and/or treating and preventing cancers by providing granzyme inhibitors to a patient.

2. Description of Related Art

Diseases caused as a result of viral infections pose a worldwide public health problem. For example, infection by the human immunodeficiency virus (HIV), alone is currently responsible for an estimated 36.1 million people worldwide living with acquired immune deficiency syndrome (AIDS). HIV is exemplified by several viral strains such as HIV-1 and HIV-2. In addition to HIV, other viruses such as, HCV, HTLV-1, HTLV-2, hepatitis G, enterovirus, dengue fever virus, rabies virus, etc., also result in a wide variety of pathologies.

Cancer is another worldwide health problem and is a leading cause of death. In the United States alone cancer strikes one in two men and one in three women. Cancer cells evade recognition by the immune system and continue to proliferate, eventually leading to metastasis and death. The art presently lacks effective methods to enhance the immune system to combat cancers.

Cytotoxic T-cells (CTLs) are the major protective mechanism against intracellular pathogens (especially viruses) and tumor/cancer cells, and exert their protection by killing infected cells. CTLs provide protection against pathogens by using cytolytic molecules such as perforin and granzyme B to kill infected cells. Perforin facilitates the entry of active granzyme B into the cytoplasm where it initiates a cascade of biochemical changes that result in apoptosis of a infected cell or a tumor cell.

The engagement of T-cell receptors (TCRs) on naive CD8 cells by antigen peptide-class I major histocompatibility complexes (pMHC) leads to the proliferation and differentiation of CD8 cells into CTLs (Zinkernagel and Doherty, 1974). Cytolysis is initiated by the formation of antigen-specific conjugates that result in the lysis of pMHC presenting target cells (Zinkernagel and Doherty, 1974; Kagi et al., 1996). In CTLs, inactive granzyme B and perforin are stored in cytoplasmic granules. During cytolysis, perforin facilitates the entry of active granzyme B into the cytoplasm of targets where it initiates a cascade of biochemical changes that result in apoptosis (Kagi et al., 1994; Huesel et al., 1994).

After this effector phase, a period of death ensues during which activated CTLs undergo activation induced cell death (AICD) (Razvi and Welsh, 1995). The third phase of the CD8 response is characterized by the appearance of memory cells that persist for many years and facilitate accelerated responses upon re-exposure to antigen such as viral antigens or tumor antigens. This is due to both an increase in the frequency of antigen-specific T-cells and to qualitative changes that allow them to respond to antigen more effectively than naive cells (antigen-hyperactivity) (Ahmed and Gray, 1996).

After a CTL has damaged its target cell it can recycle to lyse new targets, thus, during the lytic process CTLs are spared from autolysis (Berke et al., 1972; Berke and Amos, 1973). Consistent with this are observations that CTLs appear to be more resistant to cytolysis than experimental targets in vitro, suggesting a mechanism by which a CTL may protect itself from self-injury (Blakely et al., 1987; Kranz and Eisen, 1987; Zanovello et al., 1989). However, under some circumstances CTLs can be killed by other CTLs, a process referred to as fratricide (Walden and Eisen, 1990; Huang et al., 1999).

It has been shown previously that post-effector $CD8^+$ cells are the precursors of memory cells (Opferman et al., 1999). This is consistent with the earlier finding that the number of CTLs that arise in response to viral infection (clonal burst size), determines the size of the pool of anti-viral memory CD8 cells (Gagliardini et al., 1994). However, the mechanism by which some CTLs escape AICD and give rise to memory cells remains unclear.

The present inventors have examined the role of cytolytic behavior on the cell fate decision made by functionally competent CTLs (Opferman et al., 2001). Memory cells were only generated from populations of CTLs that had killed little because CTLs underwent apoptosis during cytolysis through the action of effector molecules stored in lytic granules. This is consistent with observations that perforin plays a role in inducing the AICD of CTLs (Spaner et al., 1998; Spaner et al., 1999; Stepp et al., 1999; Matloubian et al, 1999). Thus, the perforin/granzyme pathway also plays a role in memory cell development.

A possible mechanism for ensuring CTL survival during cytolysis may involve the action of endogenous serine-protease inhibitors (serpins), (reviewed in Bird, 1999). More recently a human ova-serpin, PI9, has been identified in T-cells (Sun et al., 1996). P19 is a potent inhibitor of granzyme B and protects cells in vitro from perforin/granzyme killing but not Fas-mediated death (Bird et al., 1998). Although a homologue of P19, known as SPI6, has been identified in murine lymphocytes, its potential anti-apoptotic role remains to be determined (Sun et al., 1997).

Infections with certain viruses induce high zone tolerance when the intact immune system is confronted with an excessive viral burden (Ahmed et al., 1984; Moskophidis et al., 1993 a and b). High zone tolerance is thought to be due to excessive stimulation by antigen, which induces the clonal exhaustion of CTLs and attenuates the development of anti-viral memory. The end result is chronic viral persistence and in some cases generalized immunosuppression of T-cell responses (Wu-Hsieh et al., 1988). The molecular mechanism that gives rise to the attenuation of CTL responses in clonal exhaustion is unclear. Studies have implicated the CTL effector molecule perforin in the induction of CTL apoptosis that contributes to clonal exhaustion (Matloubian et al., 1999).

The effectiveness of the treatment of chronic infections by the adoptive transfer of CTLs has been hampered by ineffective generation of persistent memory CD8 cells (Brodie et al., 1999; Tan et al., 1999). In addition, the highly desirable induction of protective CTL-memory by vaccination has proved difficult (McMichael, 1998). Therefore, there is need for a better understanding as to how CTLs can eliminate virus but at the same time escape AICD. In addition, the art presently lacks an effective method to induce the immune system to provide long-term protection from viruses and other pathogens that require CTL-memory cells for elimination. Furthermore, with respect to cancers, the art lacks methods to induce CTL-mediated immunity against cancer cells.

SUMMARY OF THE INVENTION

The present invention overcomes these and other defects in the art and provides granzyme B inhibitors, such as the endogenous serpins among others, for enhancement and/or inducement of immunity. The terms "enhancement" and "enhancing" mean the increasing of immunity over a level of immunity that is already present in a subject for a short time, long time, or indefinite time. The terms "inducement" and "inducing" mean causing immunity in a subject where immunity is lacking, or at a substantially unmeasurably low level.

Thus, the invention provides methods of protection against clonal exhaustion and generation of sufficient numbers of CTL-memory cells which can provide long-term immunity. For example, this immunity can result in protection against viral infections. The invention also provides methods to enhance or induce immunity against cancers.

Therefore, provided in some embodiments, are methods for enhancing immunity comprising administering to a patient a composition comprising a granzyme inhibitor. In some embodiments, the composition comprising the granzyme inhibitor comprises an agent that can target the granzyme inhibitor to a cytotoxic T lymphocyte in a patient. The agent that targets the granzyme inhibitor to a CTL may be an antibody. As will be recognized by the skilled artisan, the antibody may be directed to a CTL-specific surface protein. For example, the antibody may be an anti-CD8 antibody. This method of targeting a granzyme inhibitor is also referred to as antifection and is described later in the specification (also see Poncet et al., 1996, incorporated herein by reference in its entirety).

In some embodiments, the granzyme inhibitor inhibits granzyme activity, inhibits granzyme transcription, inhibits granzyme translation, increases granzyme degradation, or destabilizes granzyme. In other embodiments, the granzyme inhibitor inhibits granzyme function.

The granzyme inhibitor can be a polypeptide, an anti-granzyme antibody, or a small molecule. In some specific embodiments, the polypeptide is a serpin. Serpins are endogenous serine protease inhibitors and some examples of serpin useful in the context of the present invention are SPI6, PI9, PI-6, monocyte neutrophil elastase inhibitor (MNEI), PI-8, and plasminogen activator inhibitor 2 (PAI-2).

There is no requirement that the polypeptide granzyme inhibitors of the invention comprise a full-length native polypeptide sequence. Rather, the polypeptide can also have a sequence that is modified from a native polypeptide sequence using the techniques known to those of skill in the art and/or taught in this specification. In some particular embodiments, the polypeptide is a mimetic that comprises a sequence that binds to granzyme and has granzyme inhibitory function. One example of such a mimetic would be a PI9 mimetic that comprises part or all of the sequence from PI9 that binds directly to granzyme, i.e. GTEAAASSCFVAECCMESG (SEQ. ID NO:16). This sequence contains the "reactive center" between two amino acids designated $P_1$ (the second E in SEQ ID NO:16) and $P_1'$ (the second C in SEQ ID NO:16). Sun et al. 1996. The $P_1$ residue largely dictates the specificity of serpin-proteinase binding, although those residues immediately surrounding the cleavage site also contribute to the affinity and fidelity of the interaction. It is known that, within the full serpin, $P_1$ forms a covalent bond with the granzyme which permanently inhibits the granzyme function. Those of ordinary skill in the art will understand that is be possible to reduce, increase or decrease the number of amino acids in mimetics according to the invention, so long as the active site and activity of the native polypeptide are maintained. For example, it would be possible to make a PI9 mimetic comprising 2, 3, 4, 5, 6, 7, 8, 9, 10, 11, 12, 13, 14, 15, 16, 17, 18, or 19 of the amino acids of SEQ ID NO:16. These portions of SEQ ID NO:16 can also be surrounded by additional amino acid residues in a PI9 mimetic. Of course, there are a wide variety of mimetics that can be prepared to meet the needs of the invention and the teachings of this paragraph and the remainder of the specification can be used to prepare mimetics based on a large number of polypeptides that have granzyme inhibitory activity. Those of ordinary skill in the art will, in view of the teachings of this application, prepare and test candidate mimetics for activity and utility and granzyme inhibitors. For one of ordinary skill in the art, such a mimetic is easy to make or obtain. Such mimetic peptides would be very easy for a clinician to add to the tissue culture media of blood cells drawn from a subject in order to inhibit granzyme B in the CTL cells. Alternatively, the mimetic may be administered directly to a subject.

The polypeptide granzyme inhibitors useful in the invention may, in addition to the anti-granzyme component, comprise a leader segment. Typically, these leader segments will be positively charged amino acid segments that facilitate protein translocation into the cytosol of the cell. Examples of such sequences include, but are not limited to the TAT sequences discussed elsewhere in the specification, the VP22 sequence from herpes simplex virus 1, the AntpHD sequence from *Drosophila*. Of course, it is possible for one of ordinary skill to design and test an almost unlimited number of leader sequences that can be used in the invention. In most cases, these sequences simply require a relatively short segment of primarily positively charged amino acids. For a general review of such leader sequences, one can review Ford et al. 2001.

The granzyme inhibitor may be a nucleic acid encoding a polypeptide that has granzyme inhibitory activity. For example, any of the polypeptides discussed above may be introduced into a subject via introduction of an nucleic acid encoding the polypeptide, which is then expressed to create the polypeptide.

The methods of the present invention provide enhanced immunity to a wide variety of viruses. Although not limited to any particular viral types or strains some examples of viruses to which immunity may be enhanced include HIV, LCMV, HCV, HTLV-1, HTLV-2, EBV, HBV, human cytomegalovirus, Herpes simplex 1 and 2, hepatitis G, enterovirus, dengue fever virus, rabies virus.

The methods of the present invention provide enhanced immunity to a wide variety of cancers. In some embodiments, the cancer is a cancer that escapes immune system recognition. In specific embodiments, the cancer is a melanoma, a colon cancer, a prostate cancer, a renal cancer, a non-Hodgkin lymphoma, a sarcoma, a B-cell leukemia, a lung cancer, or a breast cancer. However, any cancer may be treated by the methods set forth herein.

The methods of the invention provide enhancement of immunity by increasing the number of cytotoxic T-lymphocyte memory cells; and/or augmenting cytotoxic T-lymphocyte function; and/or augmenting cytotoxic T-lymphocyte memory cell development.

The invention also provides methods for enhancing immunity comprising expressing a granzyme inhibitor in the cytotoxic T-lymphocytes of a subject by introducing an expression construct comprising a DNA segment encoding the granzyme inhibitor under the control of a promoter active in the cytotoxic T-lymphocyte. In some embodiments, the cytotoxic T-lymphocyte is a viral specific cytotoxic T-lymphocyte.

The invention also provides methods for enhancing immunity comprising: obtaining a cytotoxic T-lymphocyte that comprises an expression vector that comprises a DNA segment encoding a granzyme inhibitor under the control of a promoter active in the cytotoxic T-lymphocyte; and administering the cytotoxic T-lymphocyte to a subject in need thereof In some embodiments, the expression vector is a viral expression construct and may be a retroviral, an adenoviral, an adeno-associated viral, a herpesviral, a polyoma viral, or a vaccinia viral construct.

The invention also provides methods for enhancing immunity comprising: obtaining a cytotoxic T-lymphocyte; exposing the cytotoxic T-lymphocyte to a leader sequence-granzyme B inhibitor fusion protein; and, administering the cytotoxic T-lymphocyte to a subject in need thereof An example of such a leader sequence is the TAT leader sequence. TAT-fusion proteins are known in the art (Dowdy et al., 1998; Schwarze et al., 1999). TAT is a HIV peptide that is highly positively charged. Thus, TAT-fusion proteins are easily uptaken by cells that are exposed to the fusion protein composition in cell culture. It is contemplated that isolated human CTL's will be isolated and exposed in culture to a leader sequence-granzyme inhibitor fusion protein, such as, for example, a leader sequence-PI9 protein or a leader sequence-PI9 mimetic. The CTL's will takeup the granzyme inhibitor and the CTL can be re-introduced into a human subject needing the therapy. In some embodiments the CTL is exposed to the leader sequence-granzyme B inhibitor fusion protein at a concentration of about 10 nM to 1000 nM. Thus, it is contemplated that concentrations such as 10 nM, 20 nM, 30 nM, 40 nM, 50 nM, 60 nM, 70 nM, 80 nM, 90 nM, 100 nM, 120 nM, 140 nM, 160 nM, 180 nM, 200 nM, 220 nM, 240 nM, 260 nM, 280 nM, 300 nM, 320 nM, 340 nM, 360 nM, 380 nM, 400 nM, 420 nM, 440 nM, 460 nM, 480 nM, 500 nM, 520 nM, 540 nM, 560 nM, 580 nM, 600 nM, 620 nM, 640 nM, 660 nM, 680 nM, 700 nM, 720 nM, 740 nM, 760 nM, 780 nM, 800 nM, 820 nM, 840 nM, 860 nM, 880 nM, 900 nM, 920 nM, 940 nM, 960 nM, 980 nM, or 1000 nM may be used. It is contemplated that intermediate concentrations in between these values may be used as well, for example, 11 nM, 25 nM, 101 nM and the like. It will also be appreciated that the exact dosage will be determined by one trained in the medical arts at the time of therapy depending on the type of disease, condition of health of the patient, age, gender and other such features.

The invention also provides methods for alleviating HIV-infection comprising: obtaining a cytotoxic T-lymphocyte that comprises an expression vector that comprises a DNA segment encoding a granzyme inhibitor under the control of a promoter active in the cytotoxic T-lymphocyte; and administering the cytotoxic T-lymphocyte to a patient in need thereof.

The methods described for the enhancement of immunity can be used in combination with other immunity enhancing or immunity inducing treatments. For example, the above- and below-described treatment of viruses may be used in conjunction with any other anti-viral treatment method known in the art. The methods for enhancing cancer immunity described above may be used in conjunction with any other anti-cancer treatment method known in the art. This includes the use of chemotherapeutic agents, radiotherapeutic agents, anti-cancer gene therapy methods, surgery and the like.

The invention also contemplates screening assays for additional granzyme B inhibitors that are useful in the context of the invention, as well as pharmaceutical compositions comprising such inhibitors and methods of treatments involving such compositions. One of ordinary skill in the art will be able to screen for such inhibitors using the teachings of this specification and the general knowledge of the art relating to such screening assays.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A & 2B. SPI6 inhibits apoptosis caused by granzyme B.

FIGS. 5A & 5B. PI-9 increases the potency of human cytolytic lymphocytes. FIG. 5A, Flow cytometric analysis of GFP in human PBLs (untransduced filled histogram) transduced with retrovirus encoding PI9 protein (forward) or controls (reverse). FIG. 5B, Mean specific lysis (±SEM, n=4) of tumor cell targets by human PBLs transduced by retrovirus over a range of effector/target (E/T) ratios.

FIGS. 6A & 6B. SPI6 Expression and leukocyte numbers in SPI6 mice. FIG. 6A, Real-time PCR was performed on cDNA from purified cells. Results are expressed as concentration of SPI6 mRNA/concentration of cyclophilin mRNA. FIG. 6B, Mean numbers (±SEM, n=3-4 mice) of lymphoid cells. Similar results were obtained with SPI6$^{+/-}$ mice from two founder lines.

FIGS. 7A, 7B, 7C, 7D, 7E, & 7F. SPI6 protects CTLs from self-inflicted damage. FIG. 7A, Lysis of CTL-targets pulsed with NP396. The mean % specific lysis (bar) of SPI6 targets was lower than that of B6 targets (p=0.006). FIG. 7B, Relative level of SPI6 mRNA in CTL-targets correlated inversely with their ability to be lysed by CTLs (r=0.744). FIG. 7C, Apoptosis of Jurkat cells transfected with SPI6 cDNA or vector alone by perforin (PFN) and human granzyme B (GRB) or by FIG. 7D, anti-human Fas mAb (anti-Fas) or γ-irradiation (γ-IR). FIG. 7E, Apoptosis of thymocytes from B6 and SPI6 mice by perforin and mouse granzyme B or by FIG. 7F, anti-mouse Fas mAb (mean ±SEM, n=3).

FIGS. 8A, 8B, 8C, & 8D. SPI6 enhances the viability and function of CTLs. FIG. 8A, The mean induction of apoptosis upon cytolysis (bar), [% apoptotic P14 CTLs with GP33 targets/% of apoptotic P14 CTLs with unpulsed targets], was lower for SPI6 CTLs compared to B6 CTLs (p=0.04). FIG. 8B, The mean lysis (±SEM, n=3 mice) of targets by P14 CTLs. FIG. 8C, Mean titers (±SEM, n=4-5 mice) of LCMV in the spleens from B6 or SPI6 mice, or FIG. 8D, CD8-deficient mice. The titer of LCMV was lower in mice reconstituted with SPI6 CD8 cells compared to those reconstituted with B6 CD8 cells (p<0.01).

FIGS. 9A, 9B, & 9C. Expression of SPI6 in anti-LCMV memory CD8 cells. FIG. 9A, FACS scans showing the presence of anti-NP396 memory CD8 cells in B6 mice. The % of positive cells after staining with anti-γ-IFN or isotype control (IC) mAbs is indicated. FIG. 9B, Anti-NP396 CD8 cells from day 8 (CTL) or day 50 (memory) B6 mice detected by tetramer staining. FIG. 9C, Relative level of SPI6 mRNA in purified CD8 cells.

FIGS. 11A, 11B, 11C, 11D, 11E, 11F, 11G, & 11I. SPI6 protects CD8 cells from AICD during differentiation of memory cells. FIG. 11A, The mean % (±SEM, n=8-12 mice) of P14 CD8 cells in the blood, number of P14 CD8 cells in the spleen after 12 FIG. 11B, or FIG. 11C, 30 days. FIG. 11D, Number of memory CD8 cells after 30 days. FIG. 11E, The mean % (±SEM, n=7-14 mice) P14 CD8 cells in the blood after LCMV infection. Number of P14 CD8 cells in the spleen after 7 (FIG. 11F), or FIG. 11G, 28 days (n=8 mice). (FIG. 11H) Number of memory CD8 cells after 30 days (n=8 mice). Mice with undetectable cells are <0.01×1 cell/mouse. In FIGS. 11B, 11C, 11D, 11F, 11G, and 11H, the mean number (bar) of cells derived from SPI6 mice was greater than that of B6 (p<0.01).

DESCRIPTION OF ILLUSTRATIVE EMBODIMENTS

Figure 1:
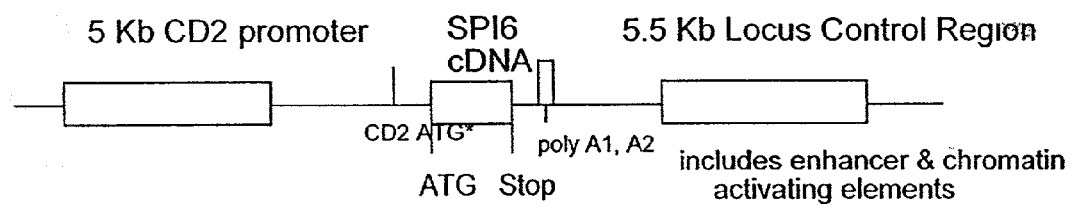
FIG. 1. The hCD2-SPI6 cassette.

Viral diseases, especially chronic viral diseases, are a challenge to the medical community. CTLs provide protection against viruses by using cytolytic molecules that include perforin and granzyme B to kill infected cells within a host. However, during severe viral infections, the CTLs are themselves killed in the process of killing infected cells. This reduces the number of CTL-memory cells that can be generated to combat future viral challenges.

The present inventors have demonstrated that, an endogenous inhibitor of granzyme B, the serine protease inhibitor 6 (SPI6) and its human homologue PI9, protects CTLs from "misdirected" granzyme B by acting as a suicide substrate. As the degree to which a CTL can resist the effects of "misdirected" granzyme B determines its life-span and hence determines the number of targets cells it can kill. The life-span of a CTL also determines its ability to generate memory CTL's required to combat future infections by the virus. These results have been facilitated by the development of a mouse model to investigate the mechanism by which a CTL cells protects itself from self-injury by granzyme B.

In addition, the present inventors have demonstrated the ability of granzyme B inhibitors to successfully eliminate virus. A transgenic mouse model of the lymphocytic choriomeningitis virus (LCMV) infection has been used to determine the role of granzyme B in controlling CTL apoptosis during memory cell development. Thus, the invention provides methods for enhancing immunity against viral infections using granzyme B inhibitors.

The present inventors also investigate the mechanism of SPI6 and other granzyme B inhibitors in preventing the clonal of exhaustion of anti-LCMV CTLs which results in a failure to eliminate virus. Also set forth are screening methods to identify other inhibitors of granzyme B that will be of therapeutic value in combating viral infections.

In addition, the invention also provides methods for enhancing immunity against cancers and/or tumors. CTL's normally participate in recognizing cancer cells and destroying them using the same perforin/granzyme pathways described above. AICD leads to reduced numbers of anti-cancer CTL's and memory-anti-cancer CTL's. Thus, the methods of the present invention that provide granzyme B inhibitors to enhance CTL function also apply to enhance-CTL's that participate in anti-cancer responses.

A. Granzymes and Granzyme Inhibitors

Natural killer cells and CTLs are the defense systems that kill cells that are either infected with virus or have transformed into tumor cells. One mechanism of killing involves exocytosis of lymphocytic granules which releases cytotoxic molecules such as performs and members of the serine protease family which are termed granzymes. The performs and granzymes together cause pores in the membrane of the attached cells. The granzymes, also known as the lymphocyte serine proteases, initiate cell death. Some potential natural substrates for granzyme B include procaspases and other proteins involved in cell death. Activated caspases then trigger a chain of biochemical events that end in apoptosis.

Research has been focused on identifying the natural substrates of granzymes (Kam et al., 2000). Although the granzyme crystal structure has not been resolved, molecular models of granzymes and synthetic substrates, such as peptide thioesters, nitroanilides and aminomethylcoumarins, have provided valuable structural information about their substrate binding sites and substrate specificity. Different granzymes have one of four primary substrate specificities: tryptase (cleaving after Arg or Lys), Asp-ase (cleaving after Asp), Met-ase (cleaving after Met or Leu), and chymase (cleaving after Phe, Tyr, or Trp) (Kam et al., 2000).

Several granzyme inhibitors are also known. Serpins are a group of naturally occurring proteins that inhibit serine proteases. For example, PI9 is a human serpin that inhibits granzyme B (see review in Bird, 1999). In addition, other synthetic inhibitors such as, isocoumarins, peptide chloromethyl ketones, and peptide phosphonates, inhibit granzymes (Kam et al., 2000).

Typically, the interaction between a glycoprotein serpin and its target serine protease leads to the formation of 1:1 covalent complex, a property that gives rise to the description of serpins as "suicide substrates". The cowpox virus serpin CrmA belongs to a group of serpins that resemble chicken ovalbumin in structure (ova-serpin). CrmA lacks an amino terminal signal peptide normally required to initiate extracellular secretion and functions within a cell to inhibit both granzyme B, and the caspases involved in cytokine maturation and apoptosis (Gagliardini et al., 1994; Miura et al., 1993).

Ova-serpins may protect CTLs from "misdirected" granzyme B and so may serve to set the threshold of not only how effectively a CTL can survive the action of its own effector molecules, but also its life-span and thus the number of cells it can kill. Thus, it is contemplated that the control of CTL viability by endogenous granzyme B inhibitors will determine (i) the number of targets a CTL can kill before dying (ii) the onset of CTL AICD, and hence, (iii) memory cell development, and (iv) clonal exhaustion.

B. Nucleic Acids

One embodiment of the present invention is to transfer nucleic acids encoding a granzyme B inhibitory polypeptide to treat or prevent viral infections and/or cancers and to enhance CTL-mediated immune responses. In some embodiments, the nucleic acids encode a full-length, substantially full-length, or functional equivalent form of a granzyme B inhibitory protein.

Thus, in some embodiments of the present invention, the treatment or prevention of viral infections and/or cancers or methods of enhancing CTL-mediated immunity involves the administration of a therapeutic nucleic acid expression construct encoding a granzyme B inhibitory polypeptide.

Certain aspects of the present invention concern a nucleic acid that encodes at least one granzyme B inhibitory polypeptide, protein, or peptide, or biologically functional equivalent thereof. In other aspects, the granzyme B inhibitory nucleic acid comprises at least one nucleic acid segment of SEQ ID NO:1, SEQ ID NO:3, or the sequence of any other granzyme B inhibitory peptide, or at least one biologically functional equivalent thereof SEQ ID NO:1 and SEQ ID NO:3 represent nucleic acids encoding the human PI9 and the mouse SPI6 respectively.

The present invention also concerns the isolation or creation of at least one recombinant construct or at least one recombinant host cell through the application of recombinant nucleic acid technology known to those of skill in the art or as described herein. The recombinant construct or host cell may comprise at least one granzyme B inhibitory nucleic acid, and may express at least one granzyme B inhibitory protein, polypeptide, or peptide, or at least one biologically functional equivalent thereof In some embodiments the invention refers to DNA sequences identified by Database Accession numbers: GenBank U71364, AF200209 or U96700.

A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. No. 5,705,629, each incorporated herein by reference. A non-limiting example of enzymatically produced nucleic acid include one produced by enzymes in amplification reactions such as PCRTm (see for example, U.S. Pat. No. 4,683,202 and U.S. Pat. No. 4,683,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g A, G, uracil "U," and C). The term "nucleic acid" encompasses the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

In certain embodiments, the nucleic acid is a nucleic acid segment. As used herein, the term "nucleic acid segment," are smaller fragments of a nucleic acid, such as for non-limiting example, those that encode only part of the granzyme B inhibitory peptide or polypeptide sequence. Thus, a "nucleic acid segment may comprise any part of the granzyme B inhibitory gene sequence, of from about 2 nucleotides to the full-length of the granzyme B inhibitory peptide- or polypeptide-encoding region. In certain embodiments, the "nucleic acid segment" encompasses the full-length granzyme B inhibitory gene sequence. In particular embodiments, the nucleic acid comprises any part of SEQ ID NO:1 or SEQ ID NO:3, of from about 2 nucleotides to the full-length of the sequence encoding SEQ ID NO:2 or SEQ ID NO:4.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended recombinant nucleic acid protocol.

a. Oligonucleotide Primers

Naturally, the present invention also encompasses DNA segments that are complementary, or essentially complementary, to the sequence set forth in SEQ ID NO:1, or SEQ ID NO:3. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 or SEQ ID NO:3, under relatively stringent conditions such as those described herein. Such sequences may encode the entire granzyme B inhibitory protein or fragments thereof.

Hybridizing fragments should be of sufficient length to provide specific hybridization to a RNA or DNA tissue sample. The use of a hybridization probe of between about 10-14 or 15-20 and about 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained.

Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 300, 500, 600, 700, 800, 900, 1000, 1100, 1200 and longer are contemplated as well. Such oligonucleotides will find use, for example, as probes in amplification reactions or in cloning experiments to add specific amino acid sequences in fusion proteins.

(i) Vectors for Delivery of Granzyme Inhibitors

Within certain embodiments, expression vectors are employed to express a granzyme B inhibitory polypeptide product, for example, a serpin such as SPI6 or PI9 in a cell. Other granzyme B inhibitors are exemplified by expression vectors encoding a peptide, polypeptide, or protein encoding an inhibitor or antagonist of granzyme B.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(a) Regulatory Elements

Throughout this application, the term "expression construct" is meant to include any type of genetic construct containing a nucleic acid coding for a gene product in which part or all of the nucleic acid encoding sequence is capable of being transcribed and translated into a polypeptide product. An "expression cassette" is defined as a nucleic acid encoding a gene product under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |

TABLE 1-continued

Promoter and/or Enhancer

| Promoter/Enhancer | References |
|---|---|
| Platelet-Derived Growth Factor (PDGF) | Pech et al., 1989 |
| Dechenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Iducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rl)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| CRP | IL-6, IL-1 | Ku & Mortensen, 1993 |

TABLE 2-continued

Inducible Elements

| Element | Iducer | References |
|---|---|---|
| SAA | IL-6, IL-1 | Jiang et al., 1995 |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | TPA | Hensel et al., 1989 |
| Thyroid Stimulating Hormone α Gene | Thyroid Hormone | Chatterjee et al., 1989 |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(b) Selectable Markers

In certain embodiments of the invention, cells, such as CTLs, contain nucleic acid constructs of the present invention. A cell containing a nucleic acid construct of the invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(c) Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

(d) Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

(e) Delivery of Expression Vectors

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

Adenovirus. One of the methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell innoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus & Horwitz, 1992; Graham and Prevec, 1991). Recently, animal studies suggested that recombinant adenovirus could be used for gene therapy (Stratford-Perricaudet & Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Adeno-Associated Viruses. Adeno-associated virus (AAV) is an attractive virus for delivering foreign genes to mammalian subjects (Ridgeway, 1988; Baichwal and Sugden, 1986; Hermonat and Muzycska, 1984). AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector of the present invention can be obtained by restriction endonuclease digestion of AAV or a plasmid such as p201, which contains a modified AAV genome (Samulski et al., 1987). Alternatively, the terminal repeats may be obtained by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

Other Viruses. Other viral vectors may be employed as expression constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-Viral Methods. Several non-viral methods for the transfer of expression constructs into mammalian cells also are contemplated by the present invention. These include lipofectamine-DNA complexes, cell sonication (Fechheimer et al., 1987), and receptor-mediated transfection (Wu and Wu, 1987; Wu and Wu, 1988).

In other embodiments of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984), successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Liposomes. In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are Lipofectamine®-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

Antifection. The invention contemplates using antibobies as a delivery vehicle to introduce genes into cells expressing specific surface antigens (Poncet et al., 1996). Antibodies directed against surface molecules on CTLs, such as CD8, can be covalently coupled to plasmids containing genes encoding granzyme B inhibitors such as PI9 or SPI6. Such conjugates can be used in vitro and in vivo to antifect (transfect using antifection) cells bearing the targeted epitope.

C. Peptides, Polypeptides, Proteins

The invention contemplates the use of a granzyme B inhibitory polypeptides in enhancing immnunit such as in the treatment or prevention of viral infections and/or cancers and in the induction of CTL-mediated immunity. In some embodiments, a full-length or a substantially full-length granzyme B inhibitory polypeptide may be used and is exemplified in non-limiting examples by serpins such as SPI6 or PI9. "Full-length" refers to a polypeptide that contains at least all the amino acids encoded by the corresponding cDNA. The term "substantially full-length" generally refers to a polypeptide that contains at least 80% of the contiguous amino acids of the full-length polypeptide. However, it is also contemplated that polypeptides containing at least about 50%, 60%, 70%, 80%, 85%, 90%, and 95% of SEQ ID NO:2, or SEQ ID NO:4, or the sequence of any other granzyme B inhibitory polypeptide are within the scope of the invention. Thus, it is contemplated that any portion of a granzyme B inhibitory polypeptide that has the granzyme inhibitory activity may be used.

The term "biologically functional equivalent" is well understood in the art and is further defined in detail herein. Accordingly, a sequence that has between about 70% and about 80%; or more preferably, between about 81% and about 90%; or even more preferably, between about 91% and about 99%; of amino acids that are identical or functionally equivalent to the amino acids of SEQ ID NO:2, or SEQ ID NO:4, or the sequence of any other granzyme B inhibitory polypeptide, will be a sequence that is "essentially as set forth in SEQ ID NO:2, or SEQ ID NO:4, or the sequence of any other granzyme B inhibitory polypeptide, provided the biological activity of the protein, polypeptide, or peptide is maintained.

The term "functionally equivalent codon" is used herein to refer to codons that encode the same amino acid, such as the six codons for arginine and serine, and also refers to codons that encode biologically equivalent amino acids (see Table 3).

It will also be understood that this invention is not limited to the particular nucleic acid of SEQ ID NO:1, or SEQ ID NO:3, or the sequence of any other nucleic acid encoding another granzyme B inhibitory polypeptide, and of the amino acid sequences of SEQ ID NO:2, or SEQ ID NO:4, or the amino acid sequence of any other granzyme B inhibitory polypeptide, respectively. Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present invention encompass biologically functional equivalent proteins, polypeptides, or peptides with granzyme B inhibitory activity. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Recombinant changes may be introduced, for example, through the application of site-directed mutagenesis techniques as discussed herein below, e.g., to introduce improvements or alterations to the antigenicity of the protein, polypeptide or peptide, or to test mutants in order to examine a granzyme B inhibitory protein, polypeptide, or peptide activity at the molecular level.

Fusion proteins, polypeptides or peptides may be prepared, e.g., where the a granzyme B inhibitory protein coding regions are aligned within the same expression unit with other proteins, polypeptides or peptides having desired functions. Non-limiting examples of such desired functions of expression sequences include purification or immunodetection purposes for the added expression sequences, e.g., proteinaceous compositions that may be purified by affinity chromatography or the enzyme labeling of coding regions, respectively.

TABLE 3

CODON TABLE

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of the protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 3 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. For example, the peptide encompassing the region of PI9 that is cleaved by and inactivates granzyme B would make an ideal mimetic to inhibit granzyme B (Sun et al., 1996). These principles may be used, in conjunction with the principles outline above, to engineer second generation molecules having many of the natural properties of a granzyme B inhibitory polypeptide, peptide or protein, but with altered and even improved characteristics. To aide in the transduction of peptide mimetics into cells the inventors contemplate including any of the leader sequences discussed above. For example, one could use the N-terminal 11 amino acid sequence from the HIV TAT protein to facilitate transduction into cells (Schwarze, et al., 1999).

(a) Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a zinc-binding domain to facilitate purification of the fusion protein. For example, the present invention envisions the use of Hexa-histidine tagged SPI6 to detect recombinant SPI6. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular leader (targeting) signals or transmembrane regions.

There is an extensive discussion of leader sequences useful in the context of the invention above. One such leader domain is encompassed within a peptide from the TAT protein of HIV which allows the entry of biologically active fusion proteins into the cytoplasm of target cells (Schwarze, et al., 1999). The use of the TAT sequence below in studies detailed below indicates the feasibility of the use of a wide variety of such sequences in the context of the invention.

(b) Protein Purification

It may be desirable to purify a granzyme B inhibitory protein or variants thereof Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "—fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "—fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature).

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

D. Antibodies

Antibodies against SPI6 will be useful reagents to examine how cells protect themselves from granzyme B in vitro and in vivo. One objective would be to immunize mice with recombinant SPI6 to generate monoclonal antibodies. This will be performed using The University of Chicago Monoclonal Antibody Core Facility, which has generated several antibodies against recombinant proteins for investigators at The University of Chicago (Chiu et al., 1999). Means for preparing and characterizing antibodies are well known in the art (See, e.g., Antibodies: A Laboratory Manual, Cold Spring Harbor Laboratory, 1988; incorporated herein by reference).

a. Antibody Generation

Antibodies to a granzyme B inhibitory polypeptide, synthetic peptide or protein may be generated using such standard techniques. Briefly, a polyclonal antibody is prepared by immunizing an animal with an immunogenic composition in accordance with the present invention and collecting antisera from that immunized animal. A wide range of animal species can be used for the production of antisera such as, a rabbit, a mouse, a rat, a hamster, a guinea pig or a goat.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bisbiazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed Mycobacterium tuberculosis), incomplete Freund's adjuvants and aluminum hydroxide adjuvant.

A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and tittering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The procured blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix or protein A followed by antigen (peptide) affinity column for purification.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified granzyme B inhibitory polypeptide, peptide or protein. The immunizing composition is administered in a manner effective to stimulate antibody producing cells. Rodents such as mice and rats are preferred animals, however, the use of rabbit, sheep, goat, monkey cells also is possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens or lymph nodes. The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Selection of the hybridoma secreting the Mab of choice is performed by culturing the cells in selective media such as HAT and individual clonal supernatants are tested (after about two to three weeks) for the desired reactivity. The assay should be sensitive, simple and rapid, such as radioimmunoassays, enzyme immunoassays, cytotoxicity assays, plaque assays, dot immunobinding assays, and the like. The selected hybridomas would then be serially diluted and cloned into individual antibody-producing cell lines, which clones can then be propagated indefinitely to provide MAbs.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens such antibodies are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867, 973 which describes antibody-therapeutic agent conjugates.

E. Animal Models

The invention demonstrates the efficacy of therapy with granzyme B inhibitors using a mouse model of viral disease and/or cancers. In some embodiments of the invention, non-human transgenic animals are produced which express SPI6. Transgenic animals expressing this marker transgene, recombinant cell lines derived from such animals and transgenic embryos may be useful in methods for screening for and identifying agents that modulate expression of SPI6.

A transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Typically, a SPI6 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

Mice are used to study the immune system because of the broad body of literature that exists concerning the use of this animal for the study of the immune system. Immunity to viral infection can only be studied in vivo. Therefore, transgenic mice infected with the well-described model virus LCMV were used herein. LCMV does not cause any pathology in mice even at doses 100-times higher than used herein. Large numbers of mice are necessary to control for mouse-to-mouse variability and to generate sufficient numbers of lymphocytes. In the embodiments concerning cancer, it is contemplated that mice-models of cancers may be used. Mice models of cancer and methods to prepare such mice models are well known to one of skill in the art.

(i) Infection with LCMV

Mice (*Mus musculus*) of the strain C57BL/6 (wild-type or SPI6-transgenic [g SPI6]) are infected with LCMV according to The University of Chicago Institutional Animal Care Use Committee (IACUC) protocol # 70687. LCMV Armstrong is injected in PBS i.p ($100 \times 1$, $2 \times 10^5$ pfu) using a 30-guage needle. LCMV Armstrong clone 13 is injected in PBS i.v. (retro-orbitally; $100 \times 1$, $10^4$-$10^6$ pfu) using a 30-gauge needle. Mice are sacrificed and the spleen removed 1-50 days after infection. The titer of LCMV and CD8 cell responses are determined.

(ii) Transduction of CTLs with Retroviral Vectors

Spleen cells from C57BL/6 mice are activated with concanavalin A for 2 days then transduced with modified MMLV that expresses epitope-tagged SPI6. After 2 days the expression of SPI6 is examined using immunofluorescence. To generate sufficient CD8-blasts, 2-4 mice are used in each experiment.

(iii) Generation of CTLs from TCR Transgenic Mice

Spleen cells from P14 TCR transgenic mice, which express the SPI6 transgene as well as from control mice that do not express the SPI6 transgene (C57BL/6/129Sv) are cultured for 3 days with GP33 peptide and IL-2 to generate anti-GP33 CTLs. Cytolytic activity is then measured by $Cr^{51}$-release assays. The onset of apoptosis in CTLs is measured by flow-cytometry.

(iv) Adoptive Transfer of CD8 Cells

Spleen cells are also purified from female C57BL/6 (wild-type or SPI6-transgenic) donor mice and CD8 cells are sorted with magnetic beads (Miltenyi Biotech) to >90% purity. Cells ($4 \times 10^6$) are then adoptively transferred to female CD8-deficient mice (C57BL/6) by i.v injection (retro-orbitally; 100 µl in PBS) using a 30-gauge needle. After 7 days mice are infected with LCMV to examine the CTL function. To purify sufficient CD8 cells each experiment requires about 40 female C57BL/6 (20 wild-type or 20 SPI6-transgenic). These cells are then transferred into 20 CD8-deficient recipients (10 transferred with wild-type CD8 cells and 10 transferred with SPI6 transgenic CD8 cells).

F. Kits for Administering Granzyme Inhibitors or Vectors Coding Therefor

The present invention also provides therapeutic kits. In some embodiment, such kits will generally contain, in suitable container means, a pharmaceutically acceptable formulation of a granzyme B inhibitor, or a vector or vectors encoding a granzyme B inhibitor in a form suitable for administration to a subject. The kits may also contain other pharmaceutically acceptable formulations, such as buffers or agents that increase gene uptake or expression.

The kits may have a single container means that contains the inhibitor or expression construct in a form suitable for administration. Other kits of the present invention include the inhibitor or expression construct expressing the inhibitor in a storage stable form, along with buffers or diluents in separate and distinct containers. For example, when the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container means.

The container means of the kit may also include at least one device for administration of the granzyme inhibitor or expression construct encoding the granzyme inhibitor. For example, a syringe or inhaler may be included. In some embodiments, the enzyme or expression construct may be pre-mixed and aliquoted into a unit dosage form and loaded into such a device. The kits may contain multiple devices for repeat administration or administration to more than one subject.

The kits of the present invention will also typically include a means for containing the vials, devices or such in close confinement for shipment, storage or commercial sale, such as, e.g., injection or blow-molded plastic containers into which the desired vials and other apparatus are placed and retained. The kits also may contain instructions for administration, including self-administration.

G. Screening for Inhibitors of Granzyme B

The present invention enables methods for identifying other inhibitors of granzyme B. Such a granzyme inhibitor may inhibit granzyme activity, inhibit granzyme transcription, inhibit granzyme translation, increase granzyme degradation, destabilize granzyme or inhibit granzyme function.

These methods may comprise random screening of large libraries of candidate substances. Alternatively, the assays may be used to focus on particular classes of compounds selected with an eye towards structural attributes that are believed to make them more likely to modulate the function of granzyme B. For example, the compounds selected for initial screening will be those with structural similarities to granzyme substrates. As SPI6 and PI9 are endogenous granzyme inhibitors which are suicide substrates it is possible that other synthetic or natural suicide substrate molecules of granzyme B will achieve the same function. By function, it is meant that one may assay for the decrease or loss of granzyme B activity.

To identify an inhibitor of granzyme B, one generally will determine the function of granzyme B in the presence and absence of the candidate substance. For example, a method generally comprises:

(a) providing a candidate inhibitor of granzyme B;
(b) admixing the candidate inhibitor with an isolated compound or cell, or a suitable experimental animal;
(c) measuring one or more characteristics of the compound, cell or animal in step (c); and
(d) comparing the characteristic measured in step (c) with the characteristic of the compound, cell or animal in the absence of said candidate inhibitor,
wherein a difference between the measured characteristics indicates that said candidate inhibitor is, indeed, a inhibitor of the compound, cell or animal.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

As used herein the term "candidate substance" refers to any molecule that may potentially inhibits granzyme B activity. The candidate substance may be a protein or fragment thereof, a small molecule, or even a nucleic acid molecule. It may prove to be the case that the most useful pharmacological compounds will be compounds that are structurally related to the serpins such as SPI6 and/or PI9. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors of granzyme B.

Other suitable inhibitors include ribozymes, and antibodies (including single chain antibodies), each of which would be specific for the target molecule. Such compounds are described in greater detail elsewhere in this document.

In addition to the inhibiting compounds initially identified, the inventors also contemplate that other sterically similar compounds may be formulated to mimic the key portions of the structure of the modulators. Such compounds, which may include peptidomimetics of peptide modulators, may be used in the same manner as the initial inhibitors.

An inhibitor according to the present invention may be one which exerts its inhibitory or activating effect upstream, downstream or directly on granzyme B including the activity and levels of granzyme B.

In vitro Assays. A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

In addition the candidate molecules will be screened for the inhibition of granzyme B enzymatic activity. The activity of granzyme B is readily assayed by detecting the hydrolysis of a chromogenic peptide substrate (Sun et al., 1997).

A technique for high throughput screening of compounds is described in WO 84/03564. Large numbers of small peptide test compounds are synthesized on a solid substrate, such as plastic pins or some other surface. Bound polypeptide is detected by various methods.

In cyto Assays. The present invention also contemplates the screening of compounds for their ability to inhibit granzyme B in cells. Various cell lines can be utilized for such screening assays, including cells specifically engineered for this purpose. For example, one may use cells that have been engineered to be defective in endogenous granzyme inhibitors, for example cells or cell lines isolated from SPI6 knockout mice. Perforin will be used to deliver granzyme B to such cell lines and the effect of each candidate granzyme B inhibitor determined (Froelich et al., 1996).

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

In vivo Assays. In vivo assays involve the use of various animal models, including transgenic animals that have been engineered to have specific defects, such as knockout animals that do not express endogenous granzyme B inhibitors. An example of such animals will be SPI6 knockout mice. The transgenic animals may also carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

The present invention provides methods of screening for a candidate substance that inhibit granzyme B. In these embodiments, the present invention is directed to a method for determining the ability of a candidate substance to inhibit the function or activity of granzyme B, generally including the steps of: administering a candidate substance to the animal; and determining the ability of the candidate substance to reduce the activity, and/or levels, and/or stability, and/or function of granzyme B.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

H. Granzyme B Inhibitor-Based Therapies and Pharmaceuticals a. Protein Therapy

One therapeutic/preventive approach to treat viral infections is the provision, to a subject, of a granzyme B inhibitory polypeptide, active fragments, synthetic peptides, mimetics or other analogs thereof The protein may be produced by recombinant expression means or, if small enough, generated by an automated peptide synthesizer. Formulations would be selected based on the route of administration and purpose including but not limited to liposomal formulations and classic pharmaceutical preparations. One such approach would involve using fusion proteins between a leader sequence, as discussed elsewhere in the application, and the PI9 granzyme B inhibitor. For example, anti-viral CTLs from infected patients or cancer patients would be treated in vitro with TAT-PI9 proteins. The such leader sequences are typically highly positively charged protein facilitates the delivery of PI9 into the cytoplasm of CTLs. These CTL's are then re-introduced into the patient where they affords protection from granzyme B.

b. Genetic-Based Therapy One of the therapeutic embodiments contemplated by the present inventors is the to provide an expression construct capable of expressing a granzyme B inhibitory polypeptide to a CTL cell such that the CTL cell escapes AICD and can continue to provide its protective effects against the viral infection and/or the cancer/tumor and additionally, can persist to provide generate memory CTL's. Because the sequence homology between the human, mouse, rat, rabbit, murine, primate and dog genes, any of these nucleic acids could be used in human therapy, as could any of the gene sequence variants which would encode the same, or a biologically equivalent polypeptide. The lengthy discussion above of expression vectors and the genetic elements employed therein is incorporated into this section by reference. Particularly preferred expression vectors are viral vectors.

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100-1000, or up to $1\times10^4$, $1\times10^5$, $1\times10^6$, $1\times10^7$, $1\times10^8$, $1\times10^9$, $1\times10^{10}$, $1\times10^{11}$, or $1\times10^{12}$ infectious particles to the patient. Similar figures may be extrapolated for liposomal or other non-viral formulations by comparing relative uptake efficiencies. Formulation as a pharmaceutically acceptable composition is discussed below.

I. Pharmaceutical Compositions

Where clinical applications are contemplated, it will be necessary to prepare pharmaceutical compositions comprising the therapeutic protein(s) (i.e., granzyme inhibitory proteins), and/or therapeutic nucleic acid(s), and/or therapeutic antibodies, and/or expression vectors, and/or virus stocks, and/or small molecule drugs, in a form appropriate for the intended application. Generally, this will entail preparing compositions that are essentially free of pyrogens, as well as other impurities that could be harmful to humans or animals.

One will generally desire to employ appropriate salts and buffers. Buffers also will be employed when recombinant cells are introduced into a patient. Aqueous compositions of the present invention comprise an effective amount of the proteins, vectors or drugs to a patient, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

Administration of these compositions according to the present invention will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. In the case of tumors/cancers the compositions may be administered intratumorally or to the tumor vasculature. Such compositions would normally be administered as pharmaceutically acceptable compositions, described supra. Direct topical administration to an affect area of the skin is also contemplated.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The composition may be formulated as a "unit dose." For example, one unit dose could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

J. Human Treatment Protocols

Based on the results of the in vivo animal studies described above, those of skill in the art will understand and predict the enormous potential for human treatment of viral infections with PI9, SPI6, other granzyme inhibitory polypeptides, anti-granzyme antibodies, small molecules, or other granzyme B inhibitors identified by the screening methods described above.

Such treatment will be particularly useful tools for the treatment of viral diseases caused by viruses such as but not limited to, HIV, HCV, HTLV-1, HTLV-2, EBV, HBV, human cytomegalovirus, Herpes simplex 1 and 2, hepatitis G, enterovirus, dengue fever virus, rabies virus. In the embodiments concerning cancer, the treatment methods of the invention are useful in the treatment of a wide variety of cancers including cancers of the bladder, blood, bone, bone marrow, brain, breast, central nervous system, colon, esophagus, gastrointestine, head, kidney, liver, lung, nasopharynx, neck, ovary, prostate, skin, stomach, or uterus.

It is expected that these clinical trials will confirm the use of granzyme B inhibitors for the treatment of viral infections in humans. Dosage and frequency regimes will initially be based on the data obtained from in vivo animal studies, as was described above.

The treatment of human viral infections or cancer is possible by the introduction of a nucleic acid encoding PI9, SPI6, or any homolog or variant thereof This may be achieved most preferably by introduction of the desired nucleic acid through the use of a viral or non-viral vector to carry the granzyme B inhibitory sequences to efficiently infect cytotoxic T-lymphocytes (CTLs) of the human. Viral vectors will preferably be an adenoviral, a retroviral, a vaccinia viral vector or adeno-associated virus. These vectors are preferred because they have been successfully used to deliver desired sequences to cells and tend to have a high infection efficiency. The transduction of anti-viral CTLs by nucleic acids encoding granzyme B inhibitors will be performed on in vitro cultures of CTLs.

A patient with a viral infection may be treated using the following protocol. Optimally the patient will exhibit adequate bone marrow function (defined as peripheral absolute granulocyte count of >2,000/mm3 and platelet count of 100,000/mm3, adequate liver function (bilirubin 1.5 mg/dl) and adequate renal function (creatinine 1.5 mg/dl).

Infected patients can be transfused with genetically engineered CTLs that express a recombinant granzyme B inhibitor in the cytoplasm. In addition, infected patients can be transfused with CTLs that have been loaded with a granzyme B inhibitor using protein transduction delivery with leader sequence fusion proteins to enhance uptake of the protein.

A granzyme B inhibitory composition of the present invention is typically administered parenterally or orally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. The granzyme B inhibitory protein, peptide, or polypeptide or a nucleic acid encoding the granzyme B inhibitory protein, peptide, or polypeptides, may be delivered to the patient before, after or concurrently with the other anti-viral or anti-cancer agents. A typical treatment course may comprise about six doses delivered over a 7 to 21 day period or more. Upon election by the clinician the regimen may be continued six doses every three weeks or on a less frequent (monthly, bimonthly, quarterly etc.) basis. Of course, these are only exemplary times for treatment, and the skilled practitioner will readily recognize that many other time-courses are possible.

The granzyme B inhibitory compositions will be provided in an amount effective to enhance immunity to a virus or a cancer. Enhancing immunity to a virus and/or cancer may comprises increasing the number of cytotoxic T-lymphocyte memory cells, augmenting cytotoxic T-lymphocyte function, and/or augmenting cytotoxic T-lymphocyte memory cell development.

Regional delivery of the granzyme B inhibitory protein, peptide, or polypeptide or a nucleic acid encoding the granzyme B inhibitory protein, peptide, or polypeptides, will be an efficient method for delivering a therapeutically effective dose to counteract the clinical disease.

Clinical responses may be defined by acceptable measure. For example, a complete response may be defined by the disappearance of all measurable disease, for example, clearance of viral titers, for at least a month. Whereas a partial response may be defined by a 50% or greater reduction of the viral titre. In the case of cancers, a complete response may be defined by the disappearance of all measurable disease, for example, clearance of cancer cells, for at least a month. Whereas a partial response may be defined by a 50% or greater reduction of the cancer or tumor.

Of course, the above-described treatment regimes may be altered in accordance with the knowledge gained from clinical trials such as those described herein. Those of skill in the art will be able to take the information disclosed in this specification and optimize treatment regimes based on the clinical trials described in the specification.

Clinical Trials. The various elements of conducting a clinical trial, including patient treatment and monitoring, will be known to those of skill in the art in light of the present disclosure. The following information is being presented as a general guideline for use in establishing the granzyme B inhibitory protein, peptide, or polypeptide or a nucleic acid encoding the granzyme B inhibitory protein, peptide, or polypeptides, in clinical trials.

Patients chosen for clinical study will have persistent viral infections that have typically failed to respond to at least one course of conventional therapy. In the embodiments concerning cancer therapy, patients chosen for clinical study will have a cancer that has failed to respond to at least one course of conventional therapy.

The administration of the granzyme B inhibitory composition by methods set forth above will be followed by monitoring disease course and evaluation of the anti-viral or anti-cancer responses of the patients.

Physical examination, viral titre measurements, measurements of cancer volume, tumor burden, etc., and other laboratory tests should, of course, be performed before treatment and at intervals of about 3-4 weeks later. Laboratory studies should include CBC, differential and platelet count, urinalysis, liver and renal function tests, coagulation profile, and any other appropriate chemistry studies to determine the extent of disease, or determine the cause of existing symptoms.

K. Example

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Methods

Flow cytometry. All fluorochrome-conjugated monoclonal antibodies (mAb) were purchased from PharMingen. CD8 cells specific for the NP396 peptide [FQPQNCQFI (SEQ ID NO:5)] were identified by staining with anti-CD8-allophococyanin (APC) mAb and streptavidin-phycoerythrin (PE) labeled H-2D$^b$ tetramers (Murali-Krishna et al., 1998; Ober et al., 2000). To detect memory phenotype CD8 cells, spleen cells were incubated with the following H-2D$^b$-restricted LCMV peptides ($10^{-6}$M): NP396, GP33 [KAVYNFATM (SEQ ID NO:6)] or NP276 [SGVENPG-GYCL (SEQ ID NO:7)] and the CD8 cells that produced γ-IFN identified by FACS (Murali-Krishna et al., 1998). P14 CD8 cells were detected by staining with anti-V$_\alpha$2-PE, V$_\beta$8.1-fluoroscein isothiocynate (FITC) and anti-CD8-APC mAbs. The background level of staining of lymphocytes from B6 and B6 CD8-deficient mice with these mAbs was 0.03 and 0.01% respectively.

Expression of SPI6. Cells were purified (70-95% homogeneity) using mAbs conjugated to magnetic beads specific for phenotypic markers (Miltenyi Biotec). T-cell blasts were generated by culturing spleen cells with concanavalin A (conA) then sorting with magnetic beads. Macrophages were generated from bone marrow cultured with medium containing macrophage colony stimulating factor. Thymocytes were purified without sorting for subsets. SPI6 mRNA was quantitated by real time PCR on cDNA using primers and probes specific for SPI6 or mouse cyclophilin (MegaBases, Inc) (Medhurst et al., 2000).

Apoptosis assays. Jurkat cells (human thymoma) were treated for 2 hours at 37° C. with human perforin at sublytic concentrations (typically 0.2 U/mL) and human granzyme B (2 μg/ml) (Froelich et al., 1996), anti-human Fas mAb (IPO-4 (Rokhlin et al., 1997), 0.12 μg/mL) or subjected to γ-irradiation (4456 rads) and apoptosis measured after 20 hours. Thymocytes were treated with perforin and recombinant mouse granzyme B (Xia et al., 1998) (50 μg/ml) for 1 hour only (Froelich et al., 1996) (to avoid high non-specific death in the low serum medium) or with anti-mouse Fas mAb (Jo2 (Ogasawara et al., 1995), 0.3 μg/ml) and cyclohexamide (30 μg/ml) for 20 hours. Apoptosis was detected by measuring the permeability of the plasma membrane of non-necrotic cells with the green dye YO-PRO-1 (Idziorek et al., 1995) (Molecular Probes).

LCMV infections. Mice were infected i.p. with $2 \times 10^5$ pfu of LCMV Armstrong, diluted from high titer stocks. The titer of viable LCMV in the spleen was determined by standard plaque assay on Vero cells (Doyle and Oldstone, 1978).

CTL Assays. Anti-LCMV CTL effectors were recovered from the spleens of B6 mice 8 days after infection. CTL-targets were generated by conA stimulation of spleen cells followed by magnetic sorting for CD8$^+$ blasts, and were labeled with $^{51}$Cr in the presence or absence of NP396 ($10^{-6}$ M) and washed extensively. Anti-LCMV CTLs and CTL-targets were incubated together at an effector:target (E/T) ratio of 50:1. Cytolysis was determined by measuring $^{51}$Cr release after 4 hours. P14 CTLs (>90% of viable cells) were generated by culturing spleen cells for 3 days with GP33 ($10^{-6}$ M) and recombinant interleukin-2 (rIL-2, 10 U/mL). They were incubated at a 1:1 E/T ratio for 4 hours with RMA (H-2$^b$) targets that had been pulsed with GP33 ($10^{-6}$ M) and washed extensively. A FACS based assay was used to detect the onset of apoptosis in P14 CTLs after incubation with targets (Opferman et al., 2001). Apoptosis in P14 CTLs was then determined by quantitating those that were YO-PRO-1 positive. In other studies, P14 CTLs were incubated with $^{51}$Cr and GP33 labeled targets over a range of E/T ratios and cytolysis measured after 6 hours.

Adoptive Transfer. Naive CD8 cells were purified splenocytes by magnetic bead sorting (90% pure) were adoptively transferred ($4 \times 10^6$ cells) to female B6 CD8-defecient mice (Fueng-Leung et al., 1991) by i.v. injection, which resulted in a partial restoration of CD8 cells numbers (4-7% of the level of B6 mice in the blood). The percentage of adoptively transferred CD8 cells that were CD44$^{hi}$ (8-10%) was no higher than CD8 cells from the blood of wild-type B6 mice. Naive P14 CD8 cells ($10^5$) or P14 CTLs ($6 \times 10^6$, >90% viability) were adoptively transferred to B6 or B6 CD8 deficient mice respectively.

EXAMPLE 2

Mouse Serpin SPI6 Protects Cells from Apoptosis by Granzyme B

Biochemical studies have demonstrated that SPI6 can form a SDS-stable complex with human granzyme B in vitro (Sun et al., 1997). This finding, in conjunction with the observation that a human homologue of SPI6 (PI9) can protect cells from human granzyme B, indicates that SPI6 may inhibit granzyme B mediated cell death. To test this finding human thymoma cells (Jurkat cells) that over express SPI6 were generated.

The cDNA encoding SPI6 was cloned into a human CD2 minigene cassette, which has been used extensively to drive the expression of genes in T-cells (Zhumabekov et al., 1995) (FIG. 1). Jurkat cells were transfected with the CD2-SPI6 cassette or CD2-cassette alone then stable clones that express SPI6 mRNA identified RT-PCR analysis (FIG. 2A). Jurkat cells expressing SPI6 gave a 1.1 kb DNA product after PCR analysis of cDNA with SPI6-specific primers.

To determine whether SPI6 can protect cells from granzyme B, apoptosis of cells was induced in vitro following incubation with purified perforin (P) and human granzyme B(G) (Froelich et al, 1996). Jurkat cells harboring CD2-alone or CD2-SPI6 cassettes were pre-pulsed with a sub-lytic concentration of human perforin (0.2 hemolytic units [HU]/ml), then incubated with human granzyme B (2 µg/ml).

After 1 hour, the onset of chromosomal DNA condensation was measured using the dye YOPRO-1 as a measure of apoptosis (Idziorek et al., 1995). Incubation of cells with a sub-lytic dose of perforin did not result in an increase in apoptosis over the level of that observed for cells incubated alone, (5% of cells YOPRO-1-positive) (FIG. 2B). When granzyme B was added with perforin, a 10-fold increase in apoptosis was observed (50% of cells YOPRO-1-positive), demonstrating that Jurkat cells were killed by the action of granzyme B. The level of death induced by granzyme B in Jurkat cells expressing SPI6 (CD2-SPI6 transfected) was about half (27% of cells YOPRO-1-positive) of that observed for cells transfected with the control cassette (CD2-alone; 50% of cells YOPRO-1-positive). Therefore the expression of SPI6 can protect cells from apoptosis induced by granzyme B.

Figure 3:
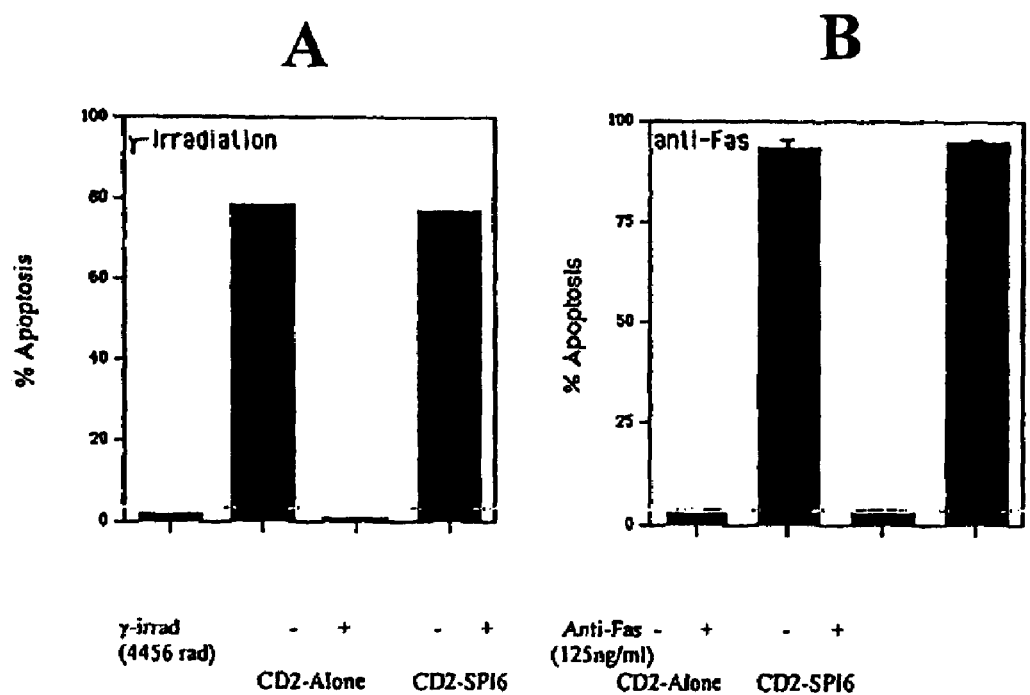
FIGS. 3A, & 3B. SPI6 does not protect against death caused by Fas-ligation or γ-irradiation.

Other mechanisms by which SPI6 may inhibit apoptosis were also studied. Following γ-irradiation (4456 rads), Jurkat cells were incubated overnight and the onset of apoptosis was measured using the dye YOPRO-1. To induce apoptosis through Fas, cells were incubated overnight with the anti-human Fas mAb IPO-4 (0.12 µg/ml) (Rokhlin et al., 1997). As shown in FIG. 3, the expression of SPI6 did not protect cells from apoptosis induced by γ-irradiation or Fas. These data indicate that SPI6 protects cells from granzyme B by direct covalent binding and inactivation (Sun et al., 1997), rather than by inactivating down-stream mediators, such as caspases, which are common to the pathways leading to apoptosis triggered by granzyme B, γ-irradiation and Fas.'

There are two conceivable mechanisms by which granzyme B may be "misdirected" into the cytoplasm or nucleus of a CTL. The first could be through fratricide in which a CTL expresses pMHC and so is a target for lysis by a neighbor (Walden and Eisen, 1990; Huang et al., 1999). The second could be a suicide mechanism in which active granzyme B somehow "leaks" into a CTL either from a granule during exocytosis, during biosynthesis or from the extra cellular medium.

To determine whether SPI6 can protect CTLs from fratricidal killing, two lines of SPI6 transgenic mice were generated, and each line was bred with C57BL/6 mice to generate separate colonies of SPI6$^{+/-}$ mice. Target CTLs can be prepared from SPI6 transgenic mice and C57BL/6 littermate controls from each colony, by culturing spleen cells for 3 days with con A and sorting with anti-CD8 magnetic beads. Target CTLs can then be pulsed with LCMV peptide antigen NP-396, during labeling with $Cr^{51}$ and washed extensively to remove unbound peptide.

As a source of effector CTLs, C57BL/6 mice can be infected with LCMV Armstrong ($2\times10^5$/mouse, i.p) and anti-LCMV CTLs purified from the spleen after 8 days. One can then determine the extent of cytolysis of $Cr^{51}$-labeled CTLs pulsed with NP-396 by anti-LCMV CTLs over a range of E:T ratios. The level of SPI6 mRNA can be measured in CTL-targets by real-time PCR. Given that CTL-targets can be generated from SPI6 transgenic mice and litter-mate controls derived from both transgenic founders the inventors expect a range of SPI6 expression in CTL-targets. The extent of lysis of CTL-targets from individual mice by anti-LCMV effector CTLs can then be compared with the level of SPI6 expression. If SPI6 serves to protect CTLs from granzyme B delivered from another CTL then one would expect the higher the expression of SPI6 in CTL targets the lower the extent of cytolysis.

EXAMPLE 3

Transgenic Mice Overexpressing SPI6 Serpin

Using standard micro-injection technology (Hogan et al., 1994), two lines of transgenic mice in the C57BL/6 strain, which harbor the SPI6 genes under the control of the CD2 promoter (FIG. 1), were produced. Stable integration of the SPI6 transgene was verified using PCR assays to screen DNA purified from tail biopsies. PCR was carried out using oligonucleotides specific for SPI6 [forward primer 5'GAATTC CGG GCT GGA TTG AGA AGCC GGA TAC 3' (SEQ ID NO:8); reverse primer 5'TGA AGA GAG AAC TCT CCC 3' (SEQ ID NO:9)]. Mice harboring transgenic SPI6 DNA were backcrossed with C57BL/6 mice. After PCR SPI6 transgenic mice ($SPI_6^{+/-}$) were distinguished from non-transgenic littermate control mice by the presence of 1.1 kb DNA product.

The level of SPI6 mRNA in lymphoid cells of SPI6 transgenic and C57BL/6 littermate controls was determined using real-time PCR. SPI6 cDNA was amplified using the following primers [forward primer 5' GCC ATC CAT CTT TTG AAG ATGC 3' (SEQ ID NO:10); reverse primer 5' TGC ACC CAA GAG AAC CAT AGC 3' (SEQ ID NO:11)] and the concentration of amplified product determined using a fluorescent probe [5' TCC AAA AAT GTA TGT TAT TCT CCT GCG AGC ATC T 3' (SEQ ID NO:12)]. The concentration of cyclophilin control mRNA as also determined [forward primer 5' CCA TCA AAC CAT TCC TTC TGT AGC 3' (SEQ ID NO:13); reverse primer 5' AGC AGA GAT TAC AGG ACA TTG CG 3' (SEQ ID NO:14); probe 5' CAG GAG AGC GTC CCT ACC CCA TCT G 3' (SEQ ID NO:15)]. The relative amount of SPI6 mRNA in each sample was then expressed as a ratio of SPI6 mRNA to cyclophilin control mRNA. In C57BL/6 control mice (B6) endogenous SPI6 expression was highest in NK cells and CD8$^+$ T-cells.

In transgenic mice (SPI6) the human CD2 promoter resulted in increased expression of SPI6 in NK cells, mature T-cells, and thymocytes. The number of T-cells in SPI6 transgenic mice was compared with C57BL/6 littermate controls (Table 1).

TABLE 1

| | Thymus | | | Spleen CD4+ | | Spleen CD8+ | | | Lymph nodes CD4+ | | Lymph nodes CD8+ | |
|---|---|---|---|---|---|---|---|---|---|---|---|---|
| | CD4+8+[30] | CD4+ | CD8+ | Total | CD44hi | Total | CD44hi | NK | Total | CD44hi | Total | CD44hi |
| B6 | 103 ± 14 | 11 ± 2 | 3.1 ± 0.4 | 3.5 ± 1.7 | 0.68 ± 0.17 | 2.2 ± 0.86 | 0.66 ± 0.13 | 0.50 ± 0.08 | 6.3 ± 1.1 | 0.73 ± 0.09 | 4.0 ± 0.58 | 0.87 ± 0.09 |
| SPI6 | 131 ± 20 | 14 ± 2 | 3.8 ± 0.4 | 4.5 ± 2.2 | 0.71 ± 0.16 | 2.9 ± 1.1 | 0.85 ± 0.06 | 0.46 ± 0.13 | 4.6 ± 0.76 | 0.64 ± 0.11 | 3.02 ± 0.7 | 0.6 ± 0.12 |

Cell Numbers (x $10^6$/mouse)

There was no significant difference in the number of immature or mature T cell subsets between SPI6 and control mice. Furthermore the number of activated (CD44$^{hi}$) or NK cells (DX5-positive) did not differ between mice.

EXAMPLE 4

SPI6 Protects Cells From Mouse Granzyme B

To examine whether SPI6 protects mouse cells against death caused by mouse granzyme B, thymocytes from SPI6 transgenic (SPI6) and C57BL/6 (B6) mice were incubated with a sub-lytic concentration of perforin (0.2 HU/ml) and various doses of recombinant mouse granzyme B (Xia et al., 1998) (a generous gift from Dr. J. Leiberman, Harvard Medical School). After one hour the onset of apoptosis was measured by determining the percentage of cells with sub-diploid DNA content. Over a range of mouse granzyme B concentrations thymocytes from SPI6 transgenic mice underwent lesser apoptosis.

However, thymocytes from SPI6 transgenic mice were no more resistant than control thymocytes from C57BL/6 mice to apoptosis induced by anti-Fas mAb (Jo2; 0.1 g/ml) binding (Ogasaware et al., 1995) or overnight in vitro culture (death by neglect). Apoptosis was measured by uptake of propidium iodide (PI). This data shows that SPI6 protects cells from granzyme B by direct covalent binding (Sun et al., 1997) rather than by inactivating down-stream mediators of apoptosis, such as caspases, which are common to other death pathways.

The ability of SPI6 to protects cells from mouse granzyme B by acting as a suicide substrate can be confirmed by numerous experiments known to one of skill in the art. For example, the formation of a covalent complex of recombinant SPI6 and granzyme B in vitro can be detected. At present no antibody available to detect SPI6 is available, hence, one can examine the interaction of purified mouse granzyme B (>99% homogeneity) (Xia et al., 1998) with purified SPI6 (>99% homogeneity). In these studies the definition of a covalent complex will be one that survives boiling with reducing agent (640 mM 2-mercaptoethanol) and SDS (2%) (Laemmli, 1970). In addition, the inventors contemplate that one may analyze the following:

(i) Inhibition of Mouse Granzyme B

As these experiments require milligram amounts of SPI6 recombinant SPI6 can be produced in *Pichia pastoris*. The inventors can modify SPI6 cDNA by PCR to incorporate a hexa-histidine (His) tag immediately after the initiating methionine and can express His-Tagged SPI6 (H-SPI6) in *Pichia pastoris*. His-Tagged SPI6 can be prepared on nickel affinity columns and eluted by 20 mM imidizole after washing in 4 mM imidazole (Sun et al., 1996). The same procedure was used to produce milligram quantities of the PI9 serpin (Sun et al., 1996). The inventors estimate that at least 5 mg (>99% homogeniety) of H-SPI6 may be purified from cultures of *Pichia pastoris*.

As a starting point, one can titrate H-SPI6 over a range of concentrations that inhibited human granzyme B (Sun et al., 1997). For inhibition studies, mouse granzyme B (10 pmol; 250 ng), can be incubated with varying concentrations of H-SPI6 (0-10 pmol; 0-400 ng) at 37° C. in 20 mM HEPES pH 7.4, 100 mM NaCl, 0.05% NP40. Residual granzyme B activity can determined after 15 minutes by a two stage assay using Boc-Ala-Ala-Asp-S-benzyl and 5,5'-dithiobis (nitrobenzoic acid) (Poe et al., 1991). If SPI6 inhibits mouse granzyme B the activity of the enzyme can diminish with increased concentrations of SPI6.

Physiologically relevant inhibition of serine protease by serpins occur with a 1:1 stiochiometry and an association rate of at least $1 \times 10^5$ $M^{-1}$ $s^{-1}$ (Sun et al., 1997). The association rate of SPI6 with human granzyme B is just out of the range for a physiologically relevant serpin:serine protease interaction (Travis and Salvesen, 1983). This may be due to differences in serpin:granzyme B specificity between mouse and man. To examine the inhibition of mouse granzyme B activity by SPI6 in more detail, one can determine the stiochiometry and association rate of serpin:serine protease interaction.

(ii) SPI6 as a Suicide Substrate of Mouse Granzyme B

To study the binding of H-SPI6 with mouse granzyme B one can use as a starting point the conditions under which SPI6 binds to human granzyme B (Sun et al., 1997). H-SPI6 (8 ng; 0.2 pmol) can be incubated with varying concentrations (0-60 ng; 0-2 pmol) of mouse granzyme B (33 kD) for 30 minutes at 37° C. in 20 mM Tris.HCl, pH 7.4, 150 mM NaCl in a volume of 10 μl. Samples can then be boiled in Laemmli buffer (Laemmli, 1970) and subjected to SDS-PAGE and visualized by silver staining. The presence of a 73 kD SDS-complex between H-SPI6 and mouse granzyme B indicates that SPI6 acts as a suicide substrate for mouse granzyme B. To control for the specificity of SPI6 binding, granzyme B can be incubated with ovalbumin, which is the prototypical ova-serpin, but does not inhibit granzyme B and so should not form a 73 kD SDS-stable complex (Bird, 1999). In addition, mixtures of SPI6 and granzyme B can be analyzed by SDS-PAGE to determine if SPI6 acts as a suicide substrate. The identification of covalent complexes between mouse granzyme B and H-SPI6 would provide a likely molecular mechanism for the protection of cells from mouse granzyme B.

(iii) Inhibition of Downstream Mediators of Granzyme B by SPI6

Alternatively or additionally, SPI6 may be involved directly in the inhibition of downstream mediators of apoptosis. Granzyme B can induce apoptosis through the activation of caspases (Darmon et al., 1995; Talanian et al., 1997). An example of an ova-serpin blocking apoptosis in this way is CrmA, which inhibits the activity of caspase 10 (Zhou et al., 1997).

The potential effects of SPI6 on downstream mediators of granzyme B may be analyzed by inducing apoptosis of Jurkat cells or thymocytes that over express SPI6 with purified perforin and granzyme B. Several caspases, namely caspases 1, 2, 3, 6, 7 and 10, are known to be targets of granzymes in vivo (Talanian et al., 1997). Activity of caspases that are activated by granzyme B can be measured using cell-permeable fluorogenic substrates and FACS in intact cells (Komoriya et al., 2000). For example, PhiPhiLux (OncoImmunin) can be used to detect the activation of caspase 3 and 7 in cells over expressing SPI6 and control cells after treatment with granzyme B and perforin.

These studies can be complimented by measuring the rate of proteolytic activation of caspases by granzyme B. Lysates from cells that overexpress SPI6 and control cells can be immunoblotted with antibodies specific for caspases (BD PharMingen, Kamiya Biotech). By detecting the lower molecular weight, activated forms of each caspase, over time, one can examine the affect of SPI6 on caspase activation by granzyme B. The ability of purified H-SPI6 to inhibit the activity of purified caspases (BD PharMingen) can also be measured in vitro. The goal of these experiments is to determine the physiologically relevant target(s) of inhibited by SPI6 that affords protection from granzyme B.

EXAMPLE 5

Production of Epitope Tagged SPI6

Earlier studies have shown that SPI6 can inactivate human granzyme B through the formation of a covalent-complex (Sun et al, 1997). For these findings to have any relevance in understanding the protection of CTLs from misdirected granzyme B, one would predict that SPI6 is located in the cytoplasm or nucleus because this is where granzyme B initiates apoptosis (Shi et al., 1997).

However the lack of an antibody to SPI6 makes it difficult to perform experiments to test these predictions. Therefore, the present inventors expressed SPI6 (mw 42 kD) with a 9 amino acid N-terminal epitope tag (FLAG) (Chubet and Brizzard, 1996; Hernan et al., 2000). Epitope tagged SPI6 (mw 43 kD) was produced following transient transfection of 293T-cells (human kidney fibroblasts) (Poe et al., 1991) with an expression plasmid encoding FLAG-SPI6 and detected in detergent extracts by immunoblotting with anti-FLAG mAb. This experiment demonstrates the feasibility of detecting SPI6 by epitope-tagging.

EXAMPLE 6

SPI6 Enhances CTL Activity and Protects from Apoptosis

Allo-specific CTLs were generated by culturing spleen cells from C57BL/6 (H-$2^b$) and C57BL/6 SPI6 transgenic mice (SPI6 mice) with irradiated BALB/c (H-$2^d$) spleen cells and IL-2. After 4 days, CTL assays were performed with P815 targets (H-$2^d$). To distinguish between target and effector cell apoptosis, target cells were identified by labeling with the green dye CFSE and CTLs by CD8 expression then FACS. The onset of apoptosis was determined by measuring the expression of phosphotidyl serine with Annexin V on the membranes of CTLs. SPI6 CTLs underwent less apoptosis during cytolysis compared to control C57BL/6 CTLs. These data show that SPI6 can protect CTLs from apoptosis induced by misdirected granzyme B during cytolysis.

In addition, allo-specific CTLs from SPI6 transgenic mice lysed more $Cr^{51}$ labeled P815 cells than C57BL/6 controls. These findings demonstrate that SPI6 protection against misdirected granzyme B improves the viability and potency of CTLs.

EXAMPLE 7

Clonal Exhaustion Induced by LCMV

Infection of C57BL/6 mice with the clone 13 variant of LCMV Armstrong induces the clonal exhaustion of CTLs and gives rise to the chronic persistence of virus (Ahmed et al., 1984; Lau et al., 1994). Compared to the parental Armstrong strain the clone 13 variant exhibits increased tropism for macrophages, which leads to increased viral dissemination, and excessive antigen burden (Matloubian et al., 1993). It is believed that the over abundance of antigen causes excessive stimulation that leads to the clonal exhaustion of CTLs. Mice were infected with LCMV Armstrong ($2 \times 10^5$ pfu, i.p.) or LCMV Armstrong clone 13 ($10^6$ pfu, i.v.), and the number of viral specific CTLs and amount of LCMV in the spleen after 8 days were determined.

LCMV Armstrong is successfully cleared from the spleen after 8 days, by a potent CTL response. In contrast, LCMV clone 13 is still present after 8 days, presumably due to a deficient CTL response. The failure to mount a CTL response can be attributed to excessive AICD of virus specific CD8 cells that results in a 10-fold lower number of NP-396 specific cells after infection with LCMV clone 13 compared to LCMV Armstrong. Furthermore, 8 days after LCMV Armstrong infection, about 7% of CD8 cells specific for NP 396, were apoptotic (based on YOPRO-1 staining), whereas 80% of these cells were undergoing apoptosis after infection with the clone 13 variant.

EXAMPLE 8

Intracellular Location of SPI6 in CD8 cells

Granzyme B is stored in an inactive form within cytolplasmic granules of CD8 cells (Atkinson and Bleakley, 1995). Cytotoxic T-cells kill by delivering active granzyme B to the cytoplasm, where it activates caspases that induce apoptosis (Darmon et al., 1995). In addition, there have been reports of granzyme B inducing apoptosis by localization to the nucleus (Shi et al., 1997). For SPI6 to protect a CTL from its own granzyme B, or that delivered by a neighbor, one would predict that it is located in compartments where active granzyme is found.

Some ova-serpins (e.g. ovalbumin) use an internal signal sequence located in the first 30 amino acids to direct secretion. Thus, to avoid the possibility of interfering with any potential SPI6 may have for synthesis in the endoplasmic reticulum, a FLAG-tag will be located at the C-terminus.

A 1.1 kb fragment containing SPI6 cDNA can be cloned in frame with a C-terminal FLAG sequence into the Hind III/Cla I site of pFLAG 14 (Chubet and Brizzard, 1996; Heman et al., 2000). The expression of the C-terminal SPI6-FLAG can be verified in detergent extracts from transiently transfected 293T-cells by immunoblotting with anti- FLAG mAbs. The gene encoding C-terminal SPI6-FLAG can be cloned into a modified version of the SAMEN Moloney murine leukemia virus (MMV) retroviral vector (Clay et al., 1999). Expression of SPI6-FLAG can be driven by a hybrid 5' LTR/human Cytomegalovirus (CMV) early promoter.

Retrovirus can be produced by transient co-transfection of the 293 GP packaging cell line (Miyoshi et al., 1998) with plasmids encoding the SPI6 recombinant retrovirus (SPI6 R) and the envelope protein of Vesticular Stomatis Virus (VSV-env). Briefly, 293 GP cells (50-80% confluent in a T-75 flask) can be transfected with SPI6 R (6 µg) and VSV-env (6 µg) DNA using Lipofectamine (Gibco-BRL) then after 2 and 3 days virus can be harvested from culture supernatant, filtered and stored at −80° C. The presence of SPI6-virus in these supernatants can be verified by transducing Jurkat cells by spinoculation in polybrene (8 µg/ml) as described in (Clay et al., 1999). After 2 days the expression of SPI6 in transduced cells can be detected by real-time PCR analysis of cDNA.

Spleen cells from C57BL/6 mice can be cultured with concanavalin A (conA) under standard conditions to generate CTLs (Coligan et al., 1995). Blasting cells can be transduced with SPI6-virus by spinoculation in polybrene (8 µg/ml) on day 2 and 3 of culture. Cells can be cultured for a further 2 days to allow the expression of SPI6, then CTLs can be purified from cultures by magnetic sorting with anti-CD8 beads (Miltenyi Biotech) and stained with anti-FLAG mAb (-FITC) and analysis by FACS to reveal the presence of intracellular C-terminal SPI6-FLAG in transduced cells.

To determine whether SPI6 is secreted, one can subject tissues culture supernatant and detergent extracts from transduced CTLs to immunoaffinity chromatography on anti-FLAG columns. Elutes can be immunoblotted with anti-Flag mAb, to determine whether SPI6 is secreted.

It is conceivable that SPI6 is unstable in the extracellular medium. Thus, to further test the possibility that SPI6 is secreted pulse-chase experiments can be performed to determine whether SPI6 traffics from the endoplasmic reticulum to the golgi (Chiu et al., 1999). Briefly, CTLs that express epitope-tagged SPI6 can be labeled with $^{35}$S-methionine for 20 minutes, then chased in complete medium for various times up to 20 hours. Lysates can be immunoprecipitated with anti-FLAG mAb then digested with endoglycosidase (Endo H) and analyzed by SDS-PAGE and fluorography. The presence of Endo H sensitive SPI6 can indicate synthesis of the endoplasmic reticulum (ER). The presence of Endo H-resistant SPI6 over time can indicate traffic into the golgi and presumably cell surface expression or secretion.

The intracellular location of SPI6 can be further examined using confocal immunofluorescence microscopy (CIM). In the absence of a mAb that can detect mouse granzyme B in cells, the presence of cytolytic granules CTLs can be revealed by staining with mAb specific for mouse perforin (PI8; [14]; then anti-rat IgG-Texas Red), and with anti-FLAG mAb (-FITC ) to identify C-terminal SPI6-FLAG SPI6. Stained cells can be analyzed by CIM. Both antibodies to perforin and FLAG have been shown previously to be effective at detecting their ligands in fixed cells (Bird, 1999; Chubet and Brizzard, 1996; Hernan et al., 2000). The intracellular distribution of green fluorescence can reveal the location of tagged-SPI6 relative to granules (perforin) that can be marked by red fluorescence. Thus, if SPI6 protects CTLs from active granzyme B, the inventors expect it to be present in the cytosol or nucleus but not cytolytic granules. In addition, cells can be stained with mAbs specific for the ER (calnexin, Santa Cruz Biotech) and ceramide to mark the trans-golgi. Analysis by CIM can complement the pulse-chase experiments above to determine if SPI6 traffics through the secretory pathway. The presence of SPI6 in the plasma membrane may indicate a potential role in inhibiting granzyme B as it is taken up from the extra cellular medium.

Sub-cellular fractionation experiments have revealed that the human homologue of SPI6 (PI9) is absent cytolytic granules and is located in the cytoplasm (Sun et al., 1996). The studies described above are designed to determine whether the putative granzyme B inhibitor SPI6 is located in the cellular compartment(s) (cytoplasm and nucleus) where active granzyme B is thought to exerts its effects, or is secreted and so may protect from extracellular granzyme B.

EXAMPLE 9

Role of SPI6 in the Control of Transgenic TCR CTL Function

One can breed SPI6 transgenic mice with transgenic mice that express the P14 TCR ($V_\alpha 2$, $V_\beta 8.1$) which is specific for the LCMV GP33 peptide [KAVYNFATM (SEQ ID NO:6)] presented by H-2D$^b$. SPI6 transgenic and C57BL/6 control mice can be crossed with P14$^{+/-}$ mice (C57BL/6) to generate P14$^{+/-}$ mice, which can be identified by the presence of TCR $V_\alpha 2^+$ CD8$^+$ cells in the blood (Ashton-Rickardt et al., 1994).

One can culture P14 CD8 spleen cells ($10^6$/ml in 2 ml) from SPI6 transgenic and C57BL/6 mice with GP33 peptide ($10^{-7}$M) and rIL-2 (10 U/mL). After 3 days about 90% of viable cells in culture are P14 CD8 cells (TCR $V_\alpha 2^+$ CD8$^+$) (Ashton-Rickardt et al., 1994). These anti-GP33 CTLs can be incubated for 4 hours at a 1:1 ratio with RMA (H-2$^b$) targets that have been pulsed with GP33 ($10^{-7}$M) and washed extensively. One can adapt an earlier FACS-based method to detect the onset of apoptosis in anti-GP33 CTLs after incubation with pMHC expressing targets (Opferman et al., 2001). To distinguish between target cell and anti-GP33 CTL apoptosis, target cells (RMA, H-2$^b$) can be identified by labeling with the red vital dye PKH26 and CTLs by CD8 mAb staining. Using FACS, the onset of apoptosis in anti-GP33 CTLs can be determined by measuring the condensation of chromosomal DNA with the yellow dye YOPRO-1 on PKH26 negative CD8$^+$ cells. To control for mouse to mouse variability, one can determine the onset of apoptosis in P14 CTLs from several SPI6 and C57BL/6 control mice. Similar studies with HY and allo-specific CTLs have suggest that a 2-3 fold induction of apoptosis may be possible after a 4 hour co-culture with antigen-pulsed targets (Opferman et al., 2001).

The degree to which incubation with antigen-pulsed versus unplused targets induces the apoptosis of anti-GP33 CTLs can be determined in P14 CD8 cells from SPI6 transgenic or C57BL/6 control mice. If SPI6 protects CTLs from granzyme B during cytolysis the inventors expect the onset of apoptosis to be lower in P14 CTLs that over express SPI6.

The present inventors have shown that CTLs that over express SPI6 not only leads to improved viability during cytolysis but also to enhanced cytolysis of allo-specific targets. To examine the effect of SPI6 on CTL function one can measure that ability of P14 CTLs to lyse Cr$^{51}$-labelled targets that express pMHC. P14 CTLs from mice that express wild-type or transgenic levels of SPI6 can be generated as described above, then incubated with targets pulsed with GP33 over a range of E:T ratios. The extent of cytolysis can be measured by quantitating the release of Cr$^{51}$ after 6 hours. If the over expression of SPI6 renders CTLs more resistant to death during target cytolysis, one may determine if it also facilitates the lysis of an increased number of targets.

EXAMPLE 10

Knockout Transgenic Mice

One can investigate the role of SPI6 in CTL biology by generating SPI6-deficient mice using ES cell technology. SPI6-deficient mice can allow investigating the relative contribution granzyme B in the control of CTL fate and function. Furthermore, protection from granzyme B may play a role in other aspects of immunity to pathogens. For example, it has been suggested that the human homologue of SPI6 (PI9) protects dendritic cells from CTL killing, thereby allowing them to act as antigen-presenting cells to CD8 cells (Bladergroen et al., 2001). The use of SPI6-deficient and transgenic mice can be used to examine the role of SPI6 in antigen-presentation as well as CTL biology.

EXAMPLE 11

Expression of PI9 in human CTLs

Figure 4:
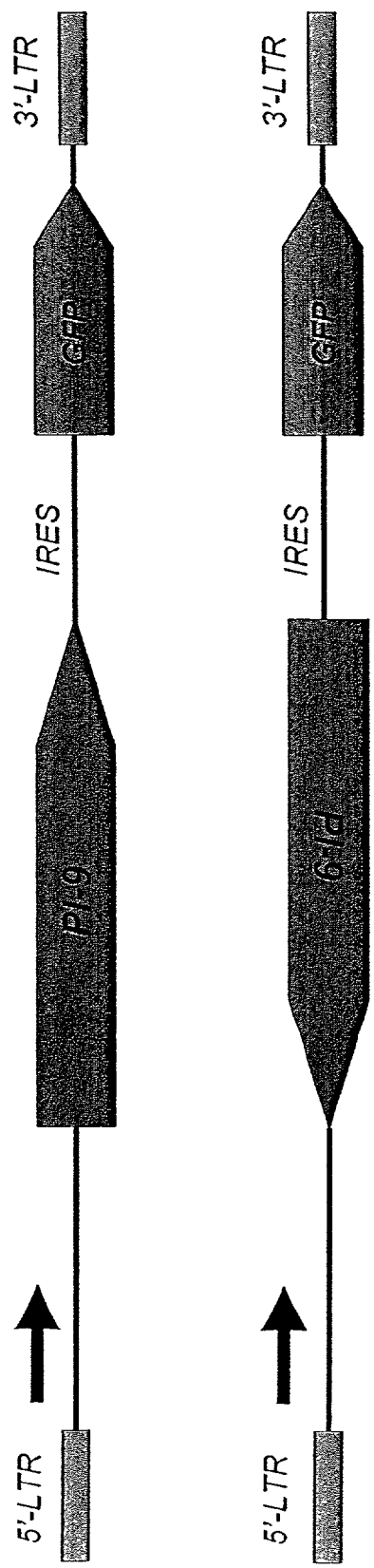
FIG. 4. Retroviral vectors. The transcription of a polycistronic message encoding PI-9 in the coding (forward) or non-coding (reverse) orientations and green fluorescent protein (GFP) was driven by sequences in the 5'-long terminal repeat (LTR) of a Molony Leukemia viral vector. An internal ribosome entry site (IRES) allowed the translation of PI9 and GFP off the polycistronic message.

Proteinase inhibitor-9 (PI9) cDNA was cloned retroviral vectors in the forward and reverse orientation (FIG. 4). The transcription of a polycistronic message encoding PI-9 in the coding (forward) or non-coding (reverse) orientations and green fluorescent protein (GFP) was driven by sequences in the 5'-long terminal repeat (LTR) of a Molony Leukemia viral vector. An internal ribosome entry site (IRES) allowed the translation of PI9 and GFP off the polycistronic message. Only the forward vector directs the expression of PI9 protein.

The percentage of human peripheral blood leukocytes (PBLs) transduced by each retrovirus was about the same (FIG. 5A), based on the expression of the green fluorescence protein (GFP) reporter, which is encoded on a polycistronic mRNA with PI9. Transduction with retrovirus encoding PI9 (forward) increased the ability of human cytolytic lymphocytes to kill tumor cells compared to cells transduced with the control virus (reverse) (FIG. 5B). Thus, increasing the expression of PI9 increased the ability of human cytolytic lymphocytes to tumor cells, presumably by protecting against "misdirected" granzyme B, as has been shown for the mouse homolgue SPI6.

EXAMPLE 12

Granzyme B is Involved in the Development of Memory Cells

SPI6 mice have elevated levels of SPI6 mRNA in cells of the immune system, most notably in T and NK cells, because expression of SPI6 was driven by human CD2 transcriptional elements (FIG. 6A). The over-expression of SPI6 in T cells and NK cells did not result in increased cell survival because the numbers of these cells in the thymus and peripheral lymphoid organs of SPI6 mice did not differ from B6 mice (FIG. 6B).

SPI6 Protection During Fratricide. To examine the potential protective effects of SPI6 on CTLs the role of SPI6 in protecting a CTL during fratricide was examined (Walden and Eisen, 1990). Specifically, the ability of CTLs specific for LCMV to kill CTLs from SPI6 mice pulsed with the LCMV NP396 peptide antigen was tested (Murali-Krishna et al., 1998). CTL-targets from SPI6 mice were resistant to killing by anti-NP396 CTLs (FIG. 7A). Protection from fratricide correlated with the relative expression level of SPI6 in CTL-targets generated from several SPI6 and B6 mice (FIG. 7B). Thus, SPI6 protects CTLs from self-inflicted injury. The observed protective effect of SPI6 was due to inhibition of granzyme B. In fact, SPI6 protected Jurkat cells from human granzyme B and mouse thymocytes from murine granzyme B (Froelich et al., 1996) (FIGS. 7C, 7D, 7E, and 7F). However, SPI6 did not prevent apoptosis caused by the ligation of the Fas death receptor or by γ-irradiation (FIGS. 7C, 7D, 7E, and 7F). These data indicate that protection from granzyme B by SPI6 death is not due to inhibition of downstream apoptotic mediators shared among the pathways triggered. Instead, like its human homologue—PI9 (Sun et al., 1996) SPI6 protects cells specifically from granzyme B by acting as a suicide substrate.

To assess the role of SPI6 in CTL function, SPI6 mice were crossed with B6 P14 mice (Pircher et al., 1989), which express a transgenic T-cell receptor specific for the LCMV GP33 peptide antigen presented by H-2D$^b$. The ability of P14 CTLs were compared in B6 versus SPI6 mice to lyse targets expressing GP33. To avoid the effects of GP33 binding to P14 CTLs, which would result in overt fratricide, targets were pulsed with peptide and washed extensively. In addition, a fluorescence activated cell sorting (FACS) assay allowed the discrimination between the induction of apoptosis in targets and CTLs (Opferman et al., 2001). The over-expression of SPI6 protected P14 CTLs from apoptosis induced by cytolysis (FIG. 8A). Concomitantly, an increase in the number of GP33-pulsed targets lysed by SPI6 P14 CTLs was observed (FIG. 8B). Therefore, the inventors conclude that the increase in viability of P14 CTLs from SPI6 mice leads to more potent cytolysis.

Enhanced Viral Clearance. Cytotoxic T lymphocytes protect against viruses by killing infected cells, hence the response of SPI6 mice to LCMV Armstrong was examined. Plaque assays detecting viable LCMV in the spleen revealed no difference in the kinetics of viral expansion between B6 and SPI6 mice over the first 4 days of infection. However, after 5 days when anti-LCMV CTLs are detectable, the clearance of LCMV was more rapid in SPI6 mice (FIG. 8C). For example, 6 days after infection the titer of LCMV was 6-times lower in SPI6 mice compared to B6 mice. In addition to CTLs, SPI6 is also over expressed in antigen presenting, CD4 and NK cells in transgenic mice (FIG. 6A).

In order to directly examine the function of CD8 cells from SPI6 mice, CD8-deficient mice were partially reconstituted with naive CD8 cells by adoptive transfer (Fueng-Leung et al., 1991). After 6 days, the titer of LCMV in CD8-deficient mice was about 20-times higher than in wild-type mice, demonstrating a critical role for CD8 cells in clearing LCMV (FIG. 8D). Significantly, the titer of LCMV in mice reconstituted with CD8 cells from SPI6 mice was 3-times lower than those reconstituted with CD8 cells from B6 mice. Thus, the enhanced clearance of LCMV in SPI6 mice is attributable to the increased potency of SPI6 CTLs.

Generation of Memory Cells by SPI6. Infection of B6 mice with LCMV Armstrong gives rise to long-lived memory CD8 cells, which can be detected by their ability to produce γ-IFN after ex vivo stimulation with peptide antigen (Murali-Krishna et al., 1998). Fifty days after infection of B6 mice functional memory CD8 cells specific for all LCMV peptide antigens—NP396 (FIG. 9A), GP33 and NP276 were detected. The LCMV antigen NP396 is the LCMV nucleoprotein peptide 396-404 with the sequence FQPQNGQFI (SEQ ID NO:5). Memory CD8 cells specific for NP396 were purified from the spleens of B6 mice 50 days after infection by staining with NP396/H-2D$^b$ tetramers and FACS (FIG. 9B), and the level of SPI6 mRNA compared with that of naive CD8 cells and anti-NP396 CTLs collected 8 days after infection (FIG. 9C). The level of SPI6 mRNA was 7-times higher in these memory CD8 cells compared to CTLs. Indeed, the expression of SPI6 in anti-NP396 specific CD8 memory cells from B6 mice was the highest of all the B6 leukocyte populations examined (FIG. 6A).

Figure 10:
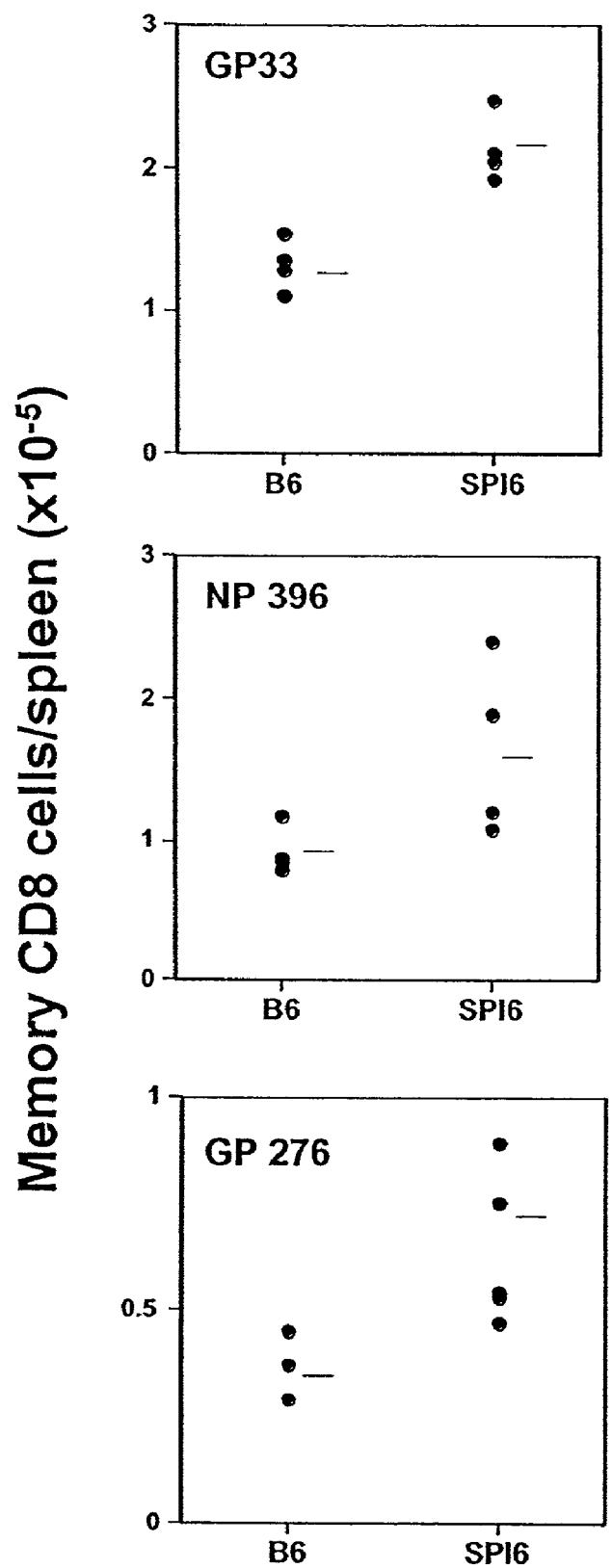
FIG. 10. Enhanced development of memory CD8 cells in SPI6 mice. The mean number (indicated by bar) of memory CD8 cells specific for 3 LCMV peptide antigens was higher in SPI6 mice compared to B6 control mice (GP33 p=0.008, NP396 p=0.03, NP276 p=0.03).

Elevated expression of SPI6 in memory CD8 cells indicate a possible role for SPI6 in protecting memory cell precursors from AICD due to granzyme B. The development of memory CD8 cells in SPI6 mice 50 days after infection with LCMV Armstrong. The number of CD8 memory cells specific for all 3 peptide antigens tested was higher in SPI6 mice compared to B6 controls (FIG. 10), thus demonstrating a role for SPI6 in the development of CD8 memory cells.

Generation of Memory Cells by Prevention of AICD. As transgenic SPI6 is expressed in lymphocytes other than CD8 cells it was investigated if the elevated number of memory cells in SPI6 mice was directly attributable to the protection of CD8 cell memory precursors from AICD. The survival of P14 CTLs, generated in vitro with GP33, was measured after adoptive transfer to B6 CD8-deficient mice. Analysis of the levels of P14 CD8 cells in recipient mice revealed that SPI6 protected P14 CTLs from AICD. After the first week, a 100-fold decrease in the percentage of P14 CD8 cells from B6 mice in the blood of recipients was observed which reduced to barely detectable levels, whereas P14 CD8 cells from SPI6 mice only declined 8-fold (FIG. 11A). This was not due to impaired homing of SPI6 P14 CD8 cells to lymphoid organs because after 12 days there was a correspondingly higher number of SPI6 P14 CD8 cells in the spleens of recipients (25-times higher than B6 P14 CD8 cells) (FIG. 11B). Protection from SPI6 P14 CD8 cells from gave rise to a dramatic increase in cell recovery from the spleen after 30 days, which was 100-times higher than that of B6 P14 CD8 cells (FIG. 11C). In addition, a corresponding increase in the number of GP33-responsive CD8 cells from SPI6 mice was observed demonstrating that these P14 CD8 cells were functionally competent and possessed a memory phenotype (FIG. 11D).

Ability of SPI6 to protect CTLs generated in vivo from AICD. Naive P14 CD8 cells were adoptively transferred to B6 mice, then after 2 days mice were infected with LCMV Armstrong. Analysis of the blood and spleens of infected B6 mice revealed that P14 CD8 cells from SPI6 mice were protected from AICD. One week after infection the percentage of SPI6 P14 CD8 cells in the blood, or absolute cell number in the spleen, was no higher than that of P14 CD8 cells from B6 control mice (FIGS. 11E and 11F). However, the level of SPI6 P14 CD8 cells detected in the blood after 14 days was about 4-times higher than B6 P14 CD8 cells. Therefore, a greater proportion of P14 CD8 cells from SPI6 mice escaped AICD; 1 in 6 compared to only 1 in 16 of P14 CD8 cells from B6 mice. Protection from AICD by SPI6 resulted in an increased number of P14 CD8 cells (FIG. 11G) and GP33-responsive memory cells in the spleens of B6 recipient mice after 28 days (FIG. 11H). Thus, SPI6 protects CTLs from AICD and so influences the proportion that escape death and, thereby, the size of the memory pool.

SPI6 enhanced memory CD8 cell development by inhibiting AICD of CTLs activated by LCMV or peptide antigen. Therefore, as has been shown for perforin, it would appear that granzyme B can induce the AICD of CTLs. Since granzyme B is a phenotypic marker for CTLs, the existence of a protein which inhibits granzyme B and increases memory cell numbers supports the linear differentiation model of CTL development which predicts that memory cells are derived from CTLs that have escaped death (Opferman et al., 1999). Further, as AICD of CD8 cells does not seem to involve the Fas death receptor (Zimmerman et al., 1996), Fas mediated apoptosis would appear unlikely to have an influence on memory cell development. It is important to note that simply increasing the viability of lymphocytes is not sufficient for enhanced memory cell formation. The expression of members of the Bcl-2 family, which promote lymphocyte survival (Sentman et al., 1991), is elevated in memory cells (Grayson et al., 2000; garcia et al., 1999). However, over-expression of these pro-survival molecules does not effect the development of memory T cells (Razvi et al., 1995; Petscher et al., 1998). The present findings point to a unique role for SPI6 in the control of memory cell differentiation by protecting CTLs from AICD through inhibition of granzyme B. One could predict that memory cell development involves the selection of CTLs that express high levels of SPI6 because they would be more likely to escape AICD. The elevated expression of SPI6 in memory CD8 cells in turn could contribute to potent cytolytic responses immediately upon contact with antigen and in addition would enhanced the number and potency of CTLs that arise from memory cells (Opferman et al., 1999; Zimmermann et al., 1996).

To escape CTL-immunity some viruses thwart target cell apoptosis by producing inhibitors of death inducing proteases (Bird, 1999). In the context of the present findings, immunity to such pathogens may be viewed as a competition between the ability of lymphocyte and pathogen to avoid succumbing to apoptosis. Enhanced protection of lymphocytes will favor immunity and, conversely, protection of pathogen will favor prolonged infection. Augmenting CTL-immunity will help alleviate chronic viral infections and cancer. Progress towards this goal will result in new immunotherapies that improve CTL function through protection from granzyme B by inhibitors similar to SPI6.

EXAMPLE 13

PI-9 Increases the Potency of Human Cytolytic Lymphocytes

To demonstrate the feasibility of augmenting CTL performance by inhibiting cytosolic granzyme B the inventors transduced human peripheral blood leukocytes (PBLs) with retrovirus expressing PI9 or a control vector that does not express PI9 because it is cloned in the reverse orientation. Transduction with retrovirus encoding PI9 (forward) increased the ability of human CTL to kill target cells compared to cells transduced with the control virus (reverse).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahmed, R & Gray, D. Immunological Memory and Protective Immunity: Understanding Their Relationship. *Science* 272, 54-60 (1996).

Ahmed, R., Salmi, A., Butler, L. D., Chiller, J. M., & Oldstone, M. B. A. Selection of genetic variants of lymphocytic choriomeningitis virus in spleens of persistently infected mice. *J. Exp. Med.* 160, 521-540 (1984).

Ashton-Rickardt, P. G., Bandeira, A., Delaney, J. R., Van Kaer, L., Pircher, H.-P., Zinkernagel, R. M., & Tonegawa, S. Evidence for a differential avidity model of T cell selection in the thymus. *Cell* 76, 651-663 (1994).

Atkinson, E. A., & Bleakley, R. C. Mechanisms of lysis by cytotoxic T-cells. *Crit. Rev. Immunol.* 15, 359-385 (1995)

Badovanic, V. P., Tvinnereim, A. R., & Harty, J. T. Regulation of antigen-specific T cell homeostasis by perforin and interferon-g. *Science* 290, 1354-1357 (2000).

Berke, G., Amos, D. B. Cytotoxic lymphocytes in the absence of detectable antibody. *Nature* 242, 237 (1973).

Berke, G., Sullivan, K. A., & Amos, D. B. Tumor immunity in vitro: destruction of a mouse ascites tumor through a cycling pathway. *Science* 177, 433 (1972).

Bird, C. H., Sutton, V. R., Sun, J., Hirst, C. E., Novak, A., Kumar, S., Trapani, J. A., & Bird, P. I. Selective Regulation of Apoptosis: the Cytotoxic Lymphocyte Serpin Proteinase Inhibitor 9 Protects against Granzyme B-Mediated Apoptosis without Perturbing the Fas Cell Death Pathway. *Mol. Cell. Biol.* 18, 6387-6398 (1998).

Bird, P. I. Linear differentiation of cytotoxic effectors into memory T lymphocytes. *Science* 283, 1745-1748 (1999).

Bird, P. I. Regulation of pro-apoptotic leukocyte granule serine proteinases by intracellular serpins. *Immunol. Cell Biol.* 77, 47-57 (1999).

Bird C H, Blink E J, Hirst C E, Buzza M S, Steele P M, Sun J, Jans D A, Bird P I, "Nucleocytoplasmic distribution of the ovalbumin serpin PI-9 requires a nonconventional nuclear import pathway and the export factor Crm1," *Mol Cell Biol.*, Aug;21(16):5396-407, 2001.

Bladergroen, B. A., Strick, M. C. M., Bovenschen, N., Berkum, O. V, Scheffer, G. L., Meijer, C. J. L. M., Hack, C. E., & Kummer, J. A. The granzyme B inhibitor, protease inhibitor 9, is mainly expressed by dendritic cells and at immune-privileged sites. *J. Immunol.* 166, 3218-3225 (2001).

Blakely, A., Gorman, K., Ostergaard, H., Svoboda, K., Chau-Ching, L., Young, D-E., & Clark, W. R. Resistance of cloned cytotoxic T lymphocytes to cell mediated cytotoxicity. *J. Exp. Med* 166, 1070-1083 (1987).

Brodie, S. J., Lewinson, D. A., Patterson, B. K., Jiyamapa, D., Kreiger, J., Corey, L., Greenberg, P. D., & Riddell, S. R. In vivo migration and function of transferred HIV-1 specific cytotoxic T-cells. *Nat Medicine* 5, 34-41 (1999).

Chiu, N. M., Chun, T., Fay, M., Mandal, M., & Wang, C-W. The majority of H2-M3 is retained intracellularly in a peptide-receptive state and traffics to the cell surface in the presence of N-formulated peptides. *J. Exp. Med* 190, 423-434 (1999).

Chubet, R. G., & Brizzard, B. L. Vectors for expression and secretion of FLAG epitope-tagged proteins in mammalian cells. *Biotechniques* 20, 136-141 (1996).

Clay, T. M., Custer, M. C., Sachs, J., Hwu, P., Rosenberg, S. A., & Nishimura, M. I. Efficient transfer of a tumor antigen-reactive TCR to human peripheral blood lymphocytes confers anti-tumor reactivity. *J. Immunol.* 163, 507-513 (1999).

Clay, T. M., Custer, M. C., Spiess, P. J., & Nishimura, M. I. Potential use of T cell receptor genes to modify hematopoietic stem cells for the gene therapy of cancer. *Path. Onc. Res.* 5, 3-15 (1999).

Coligan, J. E., Kruisbeek, A. M., Margulis, D. H., Shevach, E. M. & Strober, W. *Current Protocols in Immunology* (John Wiley and Sons, New York, 1995).

Collavo, D. Resistance of lymphokine-activated T lymphocytes to cell-mediated cytotoxicity. *Cell. Immunol.* 122, 450-460 (1989).

Darmon, A. J., Nicholson, D. W., & Bleackley, R. C. Activation of CPP32 by cytotoxic T-cell-derived granzyme B. *Nature* 377, 446-448 (1995). deletion of antiviral memory $CD8^+$ T-cells. *Eur. J. Immunol.* 28, 2978-2979 (1998).

Doyle, M. V., & Oldstone, M. B. A. Interactions between viruses and Lymphocytes. *J. Immunol.* 121, 1262-1269 (1978).

Ford, et al., Protein transduction: an alternative to genetic intervention?, *Gene Therapy*, 8, 1-4, 2001.

Froelich, C. J., Orth, K., Turboz, J., Seth, P., Gottlieb, R., Babior, B., Shah, G. M., Bleackley, R. C., Dixit, V. M., & Hanna, W. New paradigm for lymphocyte granule-mediated cytotoxicity. *J. Biol. Chem* 271, 29073-29079 (1996).

Fueng-Leung, W. P., Schiham, M. W., Rahemtulla, A., Kundig, T. M., Wollenweider, M., Potter, J., van Ewijk, W., & Mak, T. CD8 is needed for development of cytotoxic cells but not helper cells. *Cell* 65, 443-449 (1991).

Gagliardini, V., Fernandez, P-A., & Lee, R. K., et al. Prevention of vertebrate neuronal cell death by the crmA gene. *Science* 263, 826-828 (1994)

Gagliardini, V., Fernandez, P-A., Lee, R. K., et al., Virus-specific $CD8^+$ T-cell memory determined by clonal burst size. *Nature* 369, 652-654 (1994).

Hernan, R. A., et al. Multiple epitope tagged expressed proteins for enhanced detection. *Biotechniques* (in press) (2000).

Hogan, B., Beddington, B., Constantini, F., & Lacey, E. *Manipulating the mouse embryo: A laboratory manual* (Cold Spring Harbor Laboratory Press, 1994).

Huang, J.-F., Yang, Y., Sepulveda, H., Shi, W., Hwang, I., Peterson, P. A., Jackson, M. R., Sprent, J. & Cai, Z. TCR-Mediated Internalization of Peptide-MHC Complexes Acquired by T Cells. *Science* 286, 952-954 (1999).

Huesel, J. W., Wesselschmidt, S., Shresta, J. H., Russell, J. H., & Ley, T. J., Cytotoxic lymphocytes require granzyme B for the rapid induction of DNA fragmentation and apoptosis in allogeneic target cells. *Cell* 76, 977-987 (1994).

Idziorek, T., Estaquier, J., DeBels, F., & Ameisen, J-C., YOPRO-1 permits cytofluorometric analysis of programmed cell death (apoptosis) without interfering with cell viability. *J. Immunol. Methods* 185, 249-258 (1995).

Kagi, D., Ledermann, B., Burki, K., Seiler, P., Odermatt, B., Olsen, K. J., Podack, Zinkernagel, R. M., & Hengartner, H. Cytotoxicity mediated by T-cells and natural killer cells is greatly impaired in perforin-deficient mice. *Nature* 369, 31-37 (1994).

Kagi, Ledermann, Burki, Zinkernagel, Hengartner, "Molecular mechanisms of lymphocyte-mediated cytotoxicity and their role in immunological protection and pathogenesis in vivo," *Ann. Rev. Immunol.*, 14:207-232, 1996.

Kam C M, Hudig D, Powers J C, "Granzymes (lymphocyte serine proteases): characterization with natural and synthetic substrates and inhibitors," *Biochim Biophys Acta*, Mar 7; 1477(1-2):307-23, 2000.

Komoriya, A., Packard, B. Z., Brown, M. J., Wu, M-L., & Henkart, P. A. Assessment of caspase activities in intact apoptotic thymocytes using cell-permeable fluorogenic caspase substrates. *J. Exp. Med.* 191, 1819-1828 (2000).

Kranz, D. M. & Eisen, H. N. Resistance of cytotoxic T lymphocytes to lysis by a clone of cytotoxic T lymphocytes. *Proc. Natl. Acad. Sci. USA*. 84, 3375-3379 (1987).

Laemmli, E. K. Cleavage of structural proteins during the assembly of the head of bacteriophage T4. *Nature* 227, 680-685 (1970).

Lau, L. L., Jamieson, B. D., Somasundaram, T., & Ahmed, R. Cytotoxic T-cells Memory without Antigen. *Nature* 369, 648-652 (1994).

Matloubian, M., Kolhekar, S. R., Somasundaram, T., & Ahmed, R. Molecular determinants of macrophage tropism and viral persistence: importance of single amino acid changes in polymerase and glycoprotein of lymphocytic choriomeningitis virus. *J. Virol.* 67, 7340-7349 (1993).

Matloubian, M., Suresh, M., Glass, A., Galvan, M., Chow, K., Whitmore, J. K., Walsh, C. G., Clark, W. R., & Ahmed, R. A role for perforin in downregulating T-cell responses during chronic viral infection. *J. Virol.* 73, 2527-2536 (1999).

McMichael, A. Preparing for HIV vaccines that induce cytotoxic T lymphocytes. *Curr. Opin. Immunol.* 10, 379-381 (1998).

Miura, M., Zhu, H., Rotello, R., Hartwieg, E. A., & Yuan, J. Induction of apoptosis in fibroblasts by IL-1 beta-converting enzyme, a mammalian homologue of the C. elegans gene ced-3. *Cell* 75, 653-660 (1993)

Miyoshi, H., Blomer, U., Takahashi, M., Gage, F. H., & Verma, I. M. Development of a self-inactivating lentivirus vector. *J. Virol.* 72, 8150-8157 (1998).

Moskophidis, D., Lechner, F., Pircher, H., & Zinkernagel, R. M., Virus persistence in acutely infected immunocompetent mice by exhaustion of antiviral cytotoxic effector T-cells. *Nature* 362, 758-761 (1993a).

Moskophidis, D., Laine, E. & Zinkernagel, R. M. Peripheral clonal deletion of antiviral memory CD8$^+$ T-cells. *Eur. J. Immunol.* 23, 3306-3311 (1993b).

Murali-Krishna, K., Altman, J. D., Suresh, M., Sourdive, D., Zajac, A., Miller, J., Slansky, J., & Ahmed, R. Counting antigen specific CD8$^+$ T-cells: A re-evaluation of bystander activation during viral infection. *Immunity* 8, 177-187 (1998).

Murali-Krishna, K., Lau, L. L., Sambhara, S., Lemonnier, F., Altman, J.,& Ahmed, R. Persistence of Memory CD8 T Cells in MHC Class I-Deficient Mice. *Science* 286, 1377-1381 (1999).

Ober, B. T., Hu, Q., Opferman, J. T., Hagevik, S., Chiu, N., Wang, C-R., & Ashton-Rickardt, P. G. Affinity of thymic self-peptides for the TCR determines the selection of CD8$^+$ T lymphocytes in the thymus. *Int Immunol* 12, 1353-1363 (2000).

Ogasawara, J., Suda, T., & Nagata, S. Selective apoptosis of CD4$^+$ CD8$^+$ thymocytes by the anti-fas antibody. *J. Exp. Med* 181, 485-491 (1995).

Opferman, J. T., Ober, B. T., Narayanan, R., Ashton-Rickardt, P. G. Suicide induced by cytolytic activity controls the differentiation of memory CD8$^+$ T lymphocytes. *Int Immunol* 13, 101-109. (2001).

Pircher, H-P., Burki, K., Lang, R., Hengartner, H., & Zinkernagel, R. M. Tolerance induction in double specific T cell receptor transgenic mice varies with antigen. *Nature* 342, 559-561 (1989).

Pircher, H-P., Moskophidis, D., Rohrer, U., Burki, K., Hengartner, H., & Zinkernagel, R. M. Viral escape by selection of cytotoxic T cell-resistant virus variants in vivo. *Nature* 346, 624-632 (1990).

Poe, M., Blake, J. T., Boulton, D. A., Gammon, M., Sigal, N. H., Wu, J. K., & Zweerink, H. J. et al. Human cytotoxic lymphocyte granzyme B. Its purification from granules and the characterization of substrate and inhibitor specificity *J. Biol. Chem* 266, 98-103 (1991).

Poe, M., Blake, J. T., Boulton, D. A., Gammon, M., Sigal, N. H., Wu, J. K., & Zweerink, H. J. *J. Biol. Chem.* 266, 98-103 (1991).

Poncet, P., Panczak., Goupy, C., Gustafsson, K., Blanpeid, C., Chavanel, G., Hirsch, R., & Hirsch, F. *Gene Therapy.* 3, 731-738.(1996).

Razvi, E. S. & Welsh, R. M. Apoptosis in viral infections. *Adv. Virus. Res.* 45, 1-60 (1995).

Rokhlin, O., et al. Fas-mediated apoptosis in human prostatic carcinoma cell lines. *Cancer Research* 57, 1758-1766 (1997).

Schwarze, S. R., Ho, A., Vocero-Akbani, A., Dowdy, S. F. *Science* 285, 1569-1572.(1999).

Shi, L. S., Mai, S., Israel, S., Browne, K. A., Trapani, J. A., & Greenberg, A. H. Granzyme B (GraB) autonomously crosses the cell membrane and perforin initiates apoptosis and GraB nuclear localization. *J. Exp. Med* 185, 855-866 (1997).

Spaner, D., Raju, K., Rabinovich, B., & Miller, R. G. A Role for Perforin in Activation-Induced T Cell Death In Vivo: Increased Expansion of Allogeneic Perforin-Deficient T Cells in SCID mice. *J. Immunol.* 162, 1192-1199 (1999).

Spaner, D., Raju, K., Radvanyi, L. Lin, Y., & Miller, R. A Role for Perforin in Activation-Induced Cell Death. *J. Immunol.* 160, 2655-2664 (1998).

Stepp, S. E., Dufourcq-Lagelouse, R., Le Deist, F., Bhawan, S., Certain, S., Mathew, P. A., Henter, J.-I., Bennett, M., Fischer, A., de Saint Basile, G., & Kumar, V. Perforin Gene Defects in Familial Hemophagocytic Lymphohistocytosis. *Science* 286, 1957-1959 (1999).

Sun, J., Bird, C. H., Sutton, V., McDonald, L., Coughlin, P. B., De Jong, T. A., Trapani, J. A., & Bird, P. I. A Cytosolic Granzyme B Inhibitor Related to the Viral Apoptotic Regulator Cytokine Response Modifier A Is Present in Cytotoxic Lymphocytes. *J. Biol. Chem.* 271, 27802-27809 (1996).

Sun, J., Ooms, L., Bird, C. H., Sutton, V. R., Trapani, J. A., & Bird, P. I. A New Family of 10 Murine Ovalbumin Serpins Includes Two Homologs of Proteinase Inhibitor 8 and Two Homologs of the Granzyme B Inhibitor (Proteinase Inhibitor 9). *J. Biol. Chem.* 272, 15434-15441 (1997).

Surh, C. D., & Sprent, J Homeostatic T cell proliferation: How far can T-cells be activated to self-ligands. *J. Exp. Med* 192, 9-14 (2000).

Talanian, R. V., Yang, X-H., Turbov, J., Seth, P., Ghayur, T., Casiano, C. A., Orth, K., & Froelich, C. J. Granule-mediated killing: Pathways for granzyme B-initiated apoptosis. *J. Exp. Med* 186, 1323-1331 (1997).

Tan, R., Xu, X., Ogg, G. S., Hansasuta, P., Dong, T., Rostron, T., Luzzi, G., Conlon, C. P., Screaton, G. R., McMicheal, A., & Rowland-Jones, S. Rapid death of adoptively transferred T-cells in Acquired Immunodeficiency Syndrome. *Blood* 93, 1506-1510 (1999).

Tough, D. F. Borrow, P. & Sprent, J. Induction of bystander T cell proliferation by viruses and type I interferon in vivo. *Science* 272, 1947-1950 (1996).

Travis, J., & Salvesen, G. S. *Ann. Rev. Biochem.* 52, 655-709 (1983).

Walden, P. R. & Eisen, H. N. Cognate peptides induce self-destruction of CD8+ cytolytic T lymphocytes. *Proc. Natl. Acad. Sci. USA.* 87, 9015-9019 (1990).

Wu-Hsieh, B., Howard, D. H., & Ahmed, R. Virus induced immunosupression: a murine model of susceptibility to opportunistic infection. *J. Infect. Dis* 158, 232-235 (1988).

Xia, Z., Kam, C-M., Huang, C., Powers, J. C., Mandle, R. J., Stevens, R. L., & Lieberman, J. Expression and purification of enzymatically active recombinant granzyme B in a baculovirus system. *Biochem. Biophys. Res. Comm.* 243, 384-389 (1998).

Zanovello, P., Cerundolo, V., Bronte, V., Giunta, M., Panozzo, M., Biasi, G. & Zhou, Q., Snipas, S., Orth, K., Muzio, M., Dixit, V. M., & Salvesen, G. S. Target protease specificity of the viral serpin CrmA: analysis of five caspases. *J. Biol. Chem* 272, 7797-7800 (1997).

Zhumabekov, T., Corbella, P., Toliani, M., & Kioussis, D. Improved version of a human CD2 minigene based vector for T cell-specific expression in transgenic mice. *J. Immunol. Methods* 185, 133-140 (1995).

Zinkernagel and Doherty, "Restriction of in vitro T cell mediated cytotoxicity in lymphocytic choriomeningitis within a syneneic or semi-allogeneic system," *Nature*, 248:701-702, 1974.

What is claimed is:

1. A method for enhancing or inducing immunity to a viral infection comprising expressing a serpin mimetic in a cytotoxic T-lymphocytes of a subject by introducing an expression construct comprising a DNA segment encoding the serpin or serpin mimetic under the control of a promoter active in the cytotoxic T-lymphocyte, wherein the serpin or serpin mimetic is further defined as SPI6, PI-6, monocyte neutrophil elastase inhibitor (MNEI), PI-8, plasminogen activator inhibitor 2 (PAI-2), or a PI-9 mimetic.

2. The method of claim 1, wherein enhancing or inducing immunity comprises increasing the number of cytotoxic T-lymphocyte memory cells.

3. The method of claim 1, wherein enhancing or inducing immunity comprises augmenting cytotoxic T-lymphocyte function.

4. The method of claim 1, wherein enhancing or inducing immunity comprises augmenting cytotoxic T-lymphocyte memory cell development.

5. A method for enhancing or inducing immunity to a virus comprising:

a) obtaining a cytotoxic T-lymphocyte that comprises an expression vector that comprises a DNA segment encoding a serpin or a serpin mimetic under the control of a promoter active in the cytotoxic T-lymphocyte; and b) administering the cytotoxic T-lymphocyte to a subject in need thereof.

6. The method of claim 5, wherein the expression vector is a viral expression construct.

7. The method of claim 6, wherein the viral expression construct is selected from the group consisting of a retrovirus, an adenovirus, an adeno-associated virus, a herpesvirus, a polyoma virus, and a vaccinia virus.

8. The method of claim 6, wherein the vector is a retroviral vector.

9. The method of claim 5, wherein the serpin or serpin mimetic inhibits granzyme function.

10. The method of claim 5, wherein the serpin or serpin mimetic is a serpin.

11. The method of claim 5, wherein the serpin is SPI6, PI9, PI-6, monocyte neutrophil elastase inhibitor (MNEI), PI-8, plasminogen activator inhibitor 2 (PAI-2).

12. The method of claim 11, wherein the serpin is SPI6.

13. The method of claim 11, wherein the serpin is PI9.

14. The method of claim 5, wherein the virus is HIV, LCMV, HCV, HTLV-1, HTLV-2, EBV, HBV, human cytomegatovirus, Herpes simplex 1, Herpes simplex 2, hepatitis G, enterovirus, dengue fever virus, or rabies virus.

15. The method of claim 14, wherein the virus is HIV.

16. The method of claim 14, wherein the virus is LCMV.

17. The method of claim 5, wherein inducing or enhancing immunity comprises increasing the number of cytotoxic T-lymphocyte memory cells.

18. The method of claim 5, wherein inducing or enhancing immunity comprises augmenting cytotoxic T-lymphocyte function.

19. The method of claim 5, wherein inducing or enhancing immunity comprises augmenting cytotoxic T-lymphocyte memory cell development.

20. The method of claim 1, wherein the expression construct is a viral expression construct.

21. The method of claim 20, wherein the viral expression construct is selected from the group consisting of a retrovirus, an adenovirus, an adeno-associated virus, a herpesvirus, a polyoma virus, and a vaccinia virus.

22. The method of claim 21, wherein the expression construct comprises a retroviral vector.

23. The method of claim 1, wherein the serpin or serpin mimetic inhibits granzyme function.

24. The method of claim 1, wherein the serpin or serpin mimetic is a serpin.

25. The method of claim 1, wherein the serpin is SPI6.

26. The method of claim 1, wherein the serpin is PI9.

27. The method of claim 1, wherein the virus is HIV, LCMV, HCV, HTLV-1, HTLV-2, EBV, HBV, human cytomegatovirus, Herpes simplex 1, Herpes simplex 2, hepatitis G, enterovirus, dengue fever virus, or rabies virus.

28. The method of claim 25, wherein the virus is HIV.

29. The method of claim 25, wherein the virus is LCMV.

30. The method of claim 5, wherein the serpin or serpin mimetic is PI9 or a PI9 mimetic.

\* \* \* \* \*

SEQUENCE LISTING

<160> NUMBER OF SEQ ID NOS: 16

<210> SEQ ID NO 1
<211> LENGTH: 1626
<212> TYPE: DNA
<213> ORGANISM: Homo sapiens

<400> SEQUENCE: 1

```
gaattccggt gaagttgacc gggtccaccc gaagcttgtg cgcgtgcagg tcgctcaggg      60
cggacgcggc acggagacgg cggcagcctg gactaggtgg caggccctgc atcatggaaa     120
ctctttctaa tgcaagtggt acttttgcca tacgcctttt aaagatactg tgtcaagata     180 accettcgca caacgtgttc tgttctcctg tgagcatctc ctctgccctg gccatggttc     240
tcctaggggc aaagggaaac accgcaaccc agatggccca ggcactgtct ttaaacacag     300
aggaagacat tcatcgggct ttccagtcgc ttctcactga agtgaacaag gctggcacac     360
agtacctgct gagaacggcc aacaggctct ttggagagaa aacttgtcag ttcctctcaa     420
cgtttaagga atcctgtctt caattctacc atgctgagct gaaggagctt tcctttatca     480
gagctgcaga agagtccagg aaacacatca cacctgggt ctcaaaaaag accgaaggta     540
aaattgaaga gttgttgccg ggtagctcaa ttgatgcaga aaccaggctg gttcttgtca     600
atgccatcta cttcaaagga aagtggaatg aaccgtttga cgaaacatac acaagggaaa     660 tgcccttaa aataaaccag gaggagcaaa ggccagtgca gatgatgtat caggaggcca     720
cgtttaagct cgcccacgtg ggcgaggtgc gcgcgcagct gctggagctg ccctacgcca     780
ggaaggagct gagcctgctg gtgctgctgc ctgacgacgg cgtggagctc agcacggtgg     840
aaaaaagtct cacttttgag aaactcacag cctggaccaa gccagactgt atgaagagta     900
ctgaggttga agttctcctt ccaaaattta actacaaga ggattatgac atggaatctg     960
tgcttcggca tttgggaatt gttgatgcct tccaacaggg caaggctgac ttgtcggcaa    1020
tgtcagcgga gagagacctg tgtctgtcca agttcgtgca caagagtttt gtggaggtga    1080
atgaagaagg caccgaggca gcggcagcgt cgagctgctt tgtagttgca gagtgctgca    1140
tggaatctgg ccccaggttc tgtgctgacc acccttttcct tttcttcatc aggcacaaca    1200
gagccaacag cattctgttc tgtggcaggt tctcatcgcc ataaagggtg cacttaccgt    1260
```

-continued

```
gcactcggcc atttccctct tcctgtgtcc ccagatcccc actacagctc caagaggatg    1320
ggcctagaaa gccaagtgca aagatgaggg cagattcctt acctgtctgc cctcatgatt    1380
tgccagcatg aattcatgat gctccacact cgcttatgct acttaatcag aatcttgaga    1440
aaatagacca taatgattcc ctgttgtatt aaaattgcca tcccccgaat tcccatagga    1500 tgcaagcaa agttcttcta gaattccaca tgcaattcac tctggcgacc ctgtgctttc     1560
ctgacactgc gaatacattc cttaacccgc tgcctcagtg gtaataaatg gtgctagccg    1620
gaattc                                                               1626
```

<210> SEQ ID NO 2
<211> LENGTH: 376
<212> TYPE: PRT
<213> ORGANISM: Homo sapiens

<400> SEQUENCE: 2

```
Met Glu Thr Leu Ser Asn Ala Ser Gly Thr Phe Ala Ile Arg Leu Leu
  1               5                  10                  15

Lys Ile Leu Cys Gln Asp Asn Pro Ser His Asn Val Phe Cys Ser Pro
             20                  25                  30

Val Ser Ile Ser Ser Ala Leu Ala Met Val Leu Leu Gly Ala Lys Gly
         35                  40                  45

Asn Thr Ala Thr Gln Met Ala Gln Ala Leu Ser Leu Asn Thr Glu Glu
     50                  55                  60

Asp Ile His Arg Ala Phe Gln Ser Leu Leu Thr Glu Val Asn Lys Ala
 65                  70                  75                  80

Gly Thr Gln Tyr Leu Leu Arg Thr Ala Asn Arg Leu Phe Gly Glu Lys
                 85                  90                  95

Thr Cys Gln Phe Leu Ser Thr Phe Lys Glu Ser Cys Leu Gln Phe Tyr
            100                 105                 110

His Ala Glu Leu Lys Glu Leu Ser Phe Ile Arg Ala Ala Glu Glu Ser
        115                 120                 125

Arg Lys His Ile Asn Thr Trp Val Ser Lys Lys Thr Glu Gly Lys Ile
    130                 135                 140

Glu Glu Leu Leu Pro Gly Ser Ser Ile Asp Ala Glu Thr Arg Leu Val
145                 150                 155                 160

Leu Val Asn Ala Ile Tyr Phe Lys Gly Lys Trp Asn Glu Pro Phe Asp
                165                 170                 175

Glu Thr Tyr Thr Arg Glu Met Pro Phe Lys Ile Asn Gln Glu Glu Gln
            180                 185                 190

Arg Pro Val Gln Met Met Tyr Gln Glu Ala Thr Phe Lys Leu Ala His
        195                 200                 205

Val Gly Glu Val Arg Ala Gln Leu Leu Glu Leu Pro Tyr Ala Arg Lys
    210                 215                 220

Glu Leu Ser Leu Leu Val Leu Leu Pro Asp Asp Gly Val Glu Leu Ser
225                 230                 235                 240

Thr Val Glu Lys Ser Leu Thr Phe Glu Lys Leu Thr Ala Trp Thr Lys
                245                 250                 255

Pro Asp Cys Met Lys Ser Thr Glu Val Glu Val Leu Leu Pro Lys Phe
            260                 265                 270

Lys Leu Gln Glu Asp Tyr Asp Met Glu Ser Val Leu Arg His Leu Gly
        275                 280                 285

Ile Val Asp Ala Phe Gln Gln Gly Lys Ala Asp Leu Ser Ala Met Ser
    290                 295                 300
```

-continued

```
Ala Glu Arg Asp Leu Cys Leu Ser Lys Phe Val His Lys Ser Phe Val
305                 310                 315                 320

Glu Val Asn Glu Glu Gly Thr Glu Ala Ala Ala Ser Ser Cys Phe
            325                 330                 335

Val Val Ala Glu Cys Cys Met Glu Ser Gly Pro Arg Phe Cys Ala Asp
            340                 345                 350

His Pro Phe Leu Phe Phe Ile Arg His Asn Arg Ala Asn Ser Ile Leu
            355                 360                 365

Phe Cys Gly Arg Phe Ser Ser Pro
    370                 375

<210> SEQ ID NO 3
<211> LENGTH: 1819
<212> TYPE: DNA
<213> ORGANISM: Mus musculus

<400> SEQUENCE: 3
```

```
gaattccggg ctggattgag aagccgcaac tgtgactctg catcatgaat actctgtctg      60
aaggaaatgg cacctttgcc atccatcttt tgaagatgct atgtcaaagc aaccctttcca   120
aaaatgtatg ttattctcct gcgagcatct cctctgctct agctatggtt ctcttgggtg    180
caaagggaca gacggcagtc cagatatctc aggcacttgg tttgaataaa gaggaaggca    240
tccatcaggg tttccagttg cttctcagga agctgaacaa gccagacaga aagtactctc    300
ttagagtggc caacaggctc tttgcagaca aacttgtga agtcctccaa acctttaagg     360
agtcctctct tcacttctat gactcagaga tggagcagct ctcctttgct gaagaagcag    420
aggtgtccag gcaacacata aacacatggg tctccaaaca aactgaaggt aaaattccag    480
agttgttgtc aggtggctcc gtcgattcag aaaccaggct ggttctcatc aatgccttat    540
attttaaagg aaagtggcat caaccattta caaagagta cacaatggac atgcccttta    600
aaataaacaa ggatgagaaa aggccagtgc agatgatgtg tcgtgaagac acatataacc    660
tcgcctatgt gaaggaggtg caggcgcaag tgctggtgat gccatatgaa ggaatggagc    720
tgagcttggt ggttctgctc ccagatgagg gtgtggacct cagcaaggtg aaaacaatc     780
tcacttttga gaagttaaca gcctggatgg aagcagattt tatgaagagc actgatgttg    840
aggttttcct tccaaaattt aaactccaag aggattatga catggagtct ctgtttcagc    900
gcttgggagt ggtggatgtc ttccaagagg acaaggctga cttatcagga atgtctccag    960
agagaaacct gtgtgtgtcc aagtttgttc caccagagtgt agtggagatc aatgaggaag   1020
cacagaggc tgcagcagcc tctgccatca tagaattttg ctgtgcctct tctgtcccaa     1080
cattctgtgc tgaccacccc ttccttttct tcatcaggca caacaaagca aacagcatcc    1140
tgttctgtgg caggttctca tctccataaa gacacatata ctacacaggg agagttctct    1200
cttcagtatc cctaccactc ctacagctct gtcaagatgg gcaagtaggg ggaagtcatg    1260
ttctaagatg aagacacttt ccttctctgt cagcctgatc ttataatgcc tgcattcaac    1320
tctccctgtc ttgaatgcat ctatgcccctt taccaggtta tgtctaatga tgccaaatac    1380
cttctgctat gctattgatt gatagcctag ccagtaattt atagccagtt agaactgact    1440
tgactgtgca agaatgctat aatggagcta gagagaaggc acaaacacta ggaaaggttg    1500
ctgttttgc agaggacaca gggacatttc ccaccactca catggctgct acaacctct     1560
ggaaattcca gttctgtgcc atgacttgat tcctttcttt ggcttctact ggctccagca    1620
tcctgcacat acatgtatcg tcattcagtt acacacaaac aagtaaaatt ttaaaaataa    1680
```

```
ataaaaattt aaagagagag tctaaaattt tagtaatggt tagataatag ctgctattgt    1740 gccttttca ggttttaatg tcattattct tgtgtataaa gtcaataatt tataggaaaa    1800
catcagtgcc ccggaattc                                                 1819
```

<210> SEQ ID NO 4
<211> LENGTH: 374
<212> TYPE: PRT
<213> ORGANISM: Mus musculus

<400> SEQUENCE: 4

```
Met Asn Thr Leu Ser Glu Gly Asn Gly Thr Phe Ala Ile His Leu Leu
 1               5                  10                  15

Lys Met Leu Cys Gln Ser Asn Pro Ser Lys Asn Val Cys Tyr Ser Pro
             20                  25                  30

Ala Ser Ile Ser Ser Ala Leu Ala Met Val Leu Leu Gly Ala Lys Gly
         35                  40                  45

Gln Thr Ala Val Gln Ile Ser Gln Ala Leu Gly Leu Asn Lys Glu Glu
     50                  55                  60

Gly Ile His Gln Gly Phe Gln Leu Leu Arg Lys Leu Asn Lys Pro
 65                  70                  75                  80

Asp Arg Lys Tyr Ser Leu Arg Val Ala Asn Arg Leu Phe Ala Asp Lys
                 85                  90                  95

Thr Cys Glu Val Leu Gln Thr Phe Lys Glu Ser Ser Leu His Phe Tyr
            100                 105                 110

Asp Ser Glu Met Glu Gln Leu Ser Phe Ala Glu Glu Ala Glu Val Ser
        115                 120                 125

Arg Gln His Ile Asn Thr Trp Val Ser Lys Gln Thr Glu Gly Lys Ile
    130                 135                 140

Pro Glu Leu Leu Ser Gly Gly Ser Val Asp Ser Glu Thr Arg Leu Val
145                 150                 155                 160

Leu Ile Asn Ala Leu Tyr Phe Lys Gly Lys Trp His Gln Pro Phe Asn
                165                 170                 175

Lys Glu Tyr Thr Met Asp Met Pro Phe Lys Ile Asn Lys Asp Glu Lys
            180                 185                 190

Arg Pro Val Gln Met Met Cys Arg Glu Asp Thr Tyr Asn Leu Ala Tyr
        195                 200                 205

Val Lys Glu Val Gln Ala Gln Val Leu Val Met Pro Tyr Glu Gly Met
    210                 215                 220

Glu Leu Ser Leu Val Val Leu Leu Pro Asp Glu Gly Val Asp Leu Ser
225                 230                 235                 240

Lys Val Glu Asn Asn Leu Thr Phe Glu Lys Leu Thr Ala Trp Met Glu
                245                 250                 255

Ala Asp Phe Met Lys Ser Thr Asp Val Glu Val Phe Leu Pro Lys Phe
            260                 265                 270

Lys Leu Gln Glu Asp Tyr Asp Met Glu Ser Leu Phe Gln Arg Leu Gly
        275                 280                 285

Val Val Asp Val Phe Gln Glu Asp Lys Ala Asp Leu Ser Gly Met Ser
    290                 295                 300

Pro Glu Arg Asn Leu Cys Val Ser Lys Phe Val His Gln Ser Val Val
305                 310                 315                 320

Glu Ile Asn Glu Glu Gly Thr Glu Ala Ala Ala Ser Ala Ile Ile
                325                 330                 335

Glu Phe Cys Cys Ala Ser Ser Val Pro Thr Phe Cys Ala Asp His Pro
            340                 345                 350
```

```
Phe Leu Phe Phe Ile Arg His Asn Lys Ala Asn Ser Ile Leu Phe Cys
        355                 360                 365

Gly Arg Phe Ser Ser Pro
        370

<210> SEQ ID NO 5
<211> LENGTH: 9
<212> TYPE: PRT
<213> ORGANISM: Mus musculus

<400> SEQUENCE: 5

Phe Gln Pro Gln Asn Gly Gln Phe Ile
1               5

<210> SEQ ID NO 6
<211> LENGTH: 9
<212> TYPE: PRT
<213> ORGANISM: Mus musculus

<400> SEQUENCE: 6

Lys Ala Val Tyr Asn Phe Ala Thr Met
1               5

<210> SEQ ID NO 7
<211> LENGTH: 11
<212> TYPE: PRT
<213> ORGANISM: Mus musculus

<400> SEQUENCE: 7

Ser Gly Val Glu Asn Pro Gly Gly Tyr Cys Leu
1               5                   10

<210> SEQ ID NO 8
<211> LENGTH: 31
<212> TYPE: DNA
<213> ORGANISM: Mus musculus

<400> SEQUENCE: 8
gaattccggg ctggattgag aagccggata c                              31

<210> SEQ ID NO 9
<211> LENGTH: 18
<212> TYPE: DNA
<213> ORGANISM: Mus musculus

<400> SEQUENCE: 9
tgaagagaga actctccc                                             18

<210> SEQ ID NO 10
<211> LENGTH: 22
<212> TYPE: DNA
<213> ORGANISM: Mus musculus

<400> SEQUENCE: 10
gccatccatc ttttgaagat gc                                        22

<210> SEQ ID NO 11
<211> LENGTH: 21
<212> TYPE: DNA
<213> ORGANISM: Mus musculus

<400> SEQUENCE: 11
tgcacccaag agaaccatag c                                         21
```

```
<210> SEQ ID NO 12
<211> LENGTH: 34
<212> TYPE: DNA
<213> ORGANISM: Mus musculus

<400> SEQUENCE: 12
tccaaaaatg tatgttattc tcctgcgagc atct                              34

<210> SEQ ID NO 13
<211> LENGTH: 24
<212> TYPE: DNA
<213> ORGANISM: Mus musculus

<400> SEQUENCE: 13
ccatcaaacc attccttctg tagc                                            24

<210> SEQ ID NO 14
<211> LENGTH: 23
<212> TYPE: DNA
<213> ORGANISM: Mus musculus

<400> SEQUENCE: 14
agcagagatt acaggacatt gcg                                             23

<210> SEQ ID NO 15
<211> LENGTH: 25
<212> TYPE: DNA
<213> ORGANISM: Mus musculus

<400> SEQUENCE: 15
caggagagcg tccctacccc atctg                                           25

<210> SEQ ID NO 16
<211> LENGTH: 19
<212> TYPE: PRT
<213> ORGANISM: Mus musculus

<400> SEQUENCE: 16

Gly Thr Glu Ala Ala Ala Ser Ser Cys Phe Val Ala Glu Cys Cys Met
 1               5                  10                  15

Glu Ser Gly
```